US012788591B2

(12) United States Patent
Bakstad et al.

(10) Patent No.: US 12,788,591 B2

(45) Date of Patent: Nov. 10, 2026

(54) INTERBODY SPINAL IMPLANTS

(71) Applicant: GetSet Surgical SA, Epalinges (CH)

(72) Inventors: Martin Bakstad, Wrocław (PL); Katarzyna Gonera, Lausanne (CH); Søren Skovlund, Værløse (DK); Didier Guillon-Cottard, Brignais (FR); Ole Stoklund, La Conversion (CH)

(73) Assignee: GetSet Surgical SA, Epalinges (CH)

( * ) Notice: Subject to any disclaimer, the term of this patent is extended or adjusted under 35 U.S.C. 154(b) by 0 days.

(21) Appl. No.: 19/172,917

(22) Filed: Apr. 8, 2025

(65) Prior Publication Data

US 2026/0306274 A1 Oct. 8, 2026

(51) Int. Cl.

*A61F 2/46* (2006.01)
*A61B 17/80* (2006.01)
*A61F 2/44* (2006.01)

(52) U.S. Cl.

CPC ............ *A61F 2/4611* (2013.01); *A61B 17/80* (2013.01); *A61B 17/808* (2013.01); *A61F 2/447* (2013.01)

(58) Field of Classification Search

CPC ...... A61F 2/4455–2/447; A61F 2/4611; A61B 17/80; A61B 17/808

See application file for complete search history.

(56) References Cited

U.S. PATENT DOCUMENTS

| | | | |
|---|---|---|---|
| 2,796,101 | A | 6/1957 | Hasemann et al. |
| 6,306,139 | B1 | 10/2001 | Fuentes |
| 6,558,423 | B1 | 5/2003 | Michelson |
| 7,740,658 | B2 | 6/2010 | Eckman |
| 7,811,287 | B2 | 10/2010 | Errico et al. |
| 7,901,413 | B1 | 3/2011 | Lewis |
| 8,257,436 | B2 | 9/2012 | Jackson |

(Continued)

FOREIGN PATENT DOCUMENTS

| | | | |
|---|---|---|---|
| AU | 2004296536 | A2 | 6/2005 |
| EP | 1694215 | B1 | 8/2006 |

(Continued)

OTHER PUBLICATIONS

SeaSpine, Admiral ACP Anterior Cervical Plat Surgical Technique, Copyright Date 2021, 36 Pages.

(Continued)

*Primary Examiner* — Julianna N Harvey

(74) *Attorney, Agent, or Firm* — Goff IP Law PLLC; Jared S. Goff

(57) ABSTRACT

A spinal interbody spacer can be positioned using a spinal interbody implant inserter including a spinal interbody implant connector and a depth stop while the interbody implant connector is connected to the interbody spacer and while the depth stop is connected to the interbody implant connector. After positioning the interbody spacer, the depth stop can be removed from a spinal plate path. The spinal plate can slide along the spinal plate path toward the interbody spacer while the interbody spacer is connected to the interbody implant connector and the depth stop is removed from the spinal plate path. A plate holder can be configured to hold the spinal plate to inhibit rotation of the plate holder around a central axis along the interbody implant connector relative to the interbody implant connector and relative to the spinal plate.

19 Claims, 17 Drawing Sheets

(56) References Cited

U.S. PATENT DOCUMENTS

| | | | |
|---|---|---|---|
| 8,366,774 | B1 | 2/2013 | Bruffey et al. |
| 8,419,795 | B2 | 4/2013 | Sweeney |
| 8,419,797 | B2 | 4/2013 | Biedermann et al. |
| 8,439,593 | B2 | 5/2013 | Slater et al. |
| 8,500,811 | B2 | 8/2013 | Blain et al. |
| 8,535,378 | B2 | 9/2013 | Jackson |
| 8,551,105 | B2 | 10/2013 | Blain et al. |
| 8,562,655 | B2 | 10/2013 | Butler |
| 8,613,761 | B2 | 12/2013 | Lindemann et al. |
| 8,641,765 | B2 | 2/2014 | Muhanna |
| 8,764,762 | B2 | 7/2014 | Blain et al. |
| 8,795,373 | B2 | 8/2014 | Jones et al. |
| 8,801,785 | B2 | 8/2014 | Brittan et al. |
| 8,845,649 | B2 | 9/2014 | Jackson |
| 8,845,737 | B2 | 9/2014 | Melkent et al. |
| 8,858,564 | B2 | 10/2014 | Errico et al. |
| 8,864,770 | B2 | 10/2014 | Blain et al. |
| 8,882,813 | B2 | 11/2014 | Jones et al. |
| 8,894,657 | B2 | 11/2014 | Jackson |
| 8,945,227 | B2 | 2/2015 | Kirschman |
| 8,961,607 | B2 | 2/2015 | Bucci |
| 9,005,288 | B2 | 4/2015 | McCormack et al. |
| 9,005,293 | B2 | 4/2015 | Moskowitz et al. |
| 9,114,023 | B2 | 8/2015 | Kana et al. |
| 9,119,682 | B2 | 9/2015 | Stoll et al. |
| 9,155,572 | B2 | 10/2015 | Altarac et al. |
| 9,161,842 | B2 | 10/2015 | Chin et al. |
| 9,179,952 | B2 | 11/2015 | Biedermann et al. |
| 9,180,022 | B2 | 11/2015 | Georges et al. |
| 9,192,483 | B1 | 11/2015 | Radcliffe et al. |
| 9,277,946 | B2 | 3/2016 | Hooper et al. |
| 9,375,237 | B2 | 6/2016 | Keegan et al. |
| 9,402,735 | B2 | 8/2016 | McDonough et al. |
| 9,414,935 | B2 | 8/2016 | McDonough et al. |
| 9,451,951 | B2 | 9/2016 | Sullivan et al. |
| 9,566,170 | B2 | 2/2017 | Schell et al. |
| 9,603,611 | B2 | 3/2017 | Perry |
| 9,622,875 | B2 | 4/2017 | Moskowitz et al. |
| 9,744,052 | B2 | 8/2017 | Moskowitz et al. |
| 9,814,601 | B2 | 11/2017 | Moskowitz et al. |
| 9,820,867 | B2 | 11/2017 | Tepper et al. |
| 9,826,973 | B2 | 11/2017 | Graul et al. |
| 9,867,719 | B2 | 1/2018 | Moskowitz et al. |
| 9,889,022 | B2 | 2/2018 | Moskowitz et al. |
| 9,936,984 | B2 | 4/2018 | Blain |
| 9,937,060 | B2 | 4/2018 | Fuhrer et al. |
| 9,980,826 | B2 | 5/2018 | Martynova et al. |
| 10,098,754 | B2 | 10/2018 | Larsson |
| 10,231,849 | B2 | 3/2019 | Squires et al. |
| 10,238,502 | B2 | 3/2019 | Prado et al. |
| 10,307,511 | B2 | 6/2019 | Clineff et al. |
| 10,420,653 | B2 | 9/2019 | Liu et al. |
| 10,441,328 | B2 | 10/2019 | Petit |
| 10,603,186 | B2 | 3/2020 | Bernhardt, Jr. et al. |
| 10,603,187 | B2 | 3/2020 | Laubert |
| 10,682,243 | B2 | 6/2020 | Phan et al. |
| 10,758,366 | B2 | 9/2020 | Daffinson et al. |
| 10,888,356 | B2 | 1/2021 | Beyer |
| 10,952,870 | B2 | 3/2021 | Scott-Young |
| 11,026,801 | B2 | 6/2021 | Suh et al. |
| 11,026,812 | B2 | 6/2021 | Daffinson et al. |
| 11,051,858 | B2 | 7/2021 | Salvermoser et al. |
| 11,083,593 | B1 | 8/2021 | Simonson et al. |
| 11,147,597 | B2 | 10/2021 | Jackson |
| 11,173,042 | B2 | 11/2021 | Walsh et al. |
| 11,179,245 | B2 | 11/2021 | Williams |
| 11,185,422 | B2 | 11/2021 | Bullard |
| 11,273,057 | B2 | 3/2022 | Walsh et al. |
| 11,273,058 | B2 | 3/2022 | Ouidja et al. |
| 11,278,426 | B2 | 3/2022 | Walsh et al. |
| 11,304,820 | B2 | 4/2022 | Terrell et al. |
| 11,351,038 | B2 | 6/2022 | Blain et al. |
| 11,364,056 | B2 | 6/2022 | Bullard |
| 11,382,769 | B2 | 7/2022 | Blain et al. |
| 11,389,214 | B2 | 7/2022 | Jackson |
| 11,406,511 | B2 | 8/2022 | Williams |
| 11,452,608 | B2 | 9/2022 | Zappacosta et al. |
| 11,464,649 | B2 | 10/2022 | Kang et al. |
| 11,464,651 | B2 | 10/2022 | Kang et al. |
| 11,576,785 | B1 | 2/2023 | Cummins |
| 11,622,867 | B2 | 4/2023 | Milz et al. |
| 11,628,070 | B2 | 4/2023 | Beyer |
| 11,633,290 | B2 | 4/2023 | Valkoun et al. |
| 11,638,650 | B2 | 5/2023 | Valkoun et al. |
| 11,648,039 | B2 | 5/2023 | Jackson |
| 11,654,030 | B2 | 5/2023 | Valkoun et al. |
| 11,678,998 | B2 | 6/2023 | Zappacosta et al. |
| 11,684,486 | B2 | 6/2023 | Petersheim et al. |
| 11,717,417 | B2 | 8/2023 | Petersheim et al. |
| 11,759,243 | B2 | 9/2023 | Moskowitz et al. |
| 11,771,483 | B2 | 10/2023 | Ammerman et al. |
| 11,779,378 | B2 | 10/2023 | Donald et al. |
| 11,786,377 | B2 | 10/2023 | Zappacosta et al. |
| 11,819,222 | B2 | 11/2023 | Adamo et al. |
| 11,839,555 | B2 | 12/2023 | Donahoe et al. |
| 11,844,702 | B2 | 12/2023 | Pavento et al. |
| 11,890,206 | B2 | 2/2024 | Flores et al. |
| 11,903,848 | B2 | 2/2024 | Beyer |
| 11,911,284 | B2 | 2/2024 | Huh et al. |
| 11,911,294 | B2 | 2/2024 | Ouidja et al. |
| 11,938,036 | B2 | 3/2024 | Blain et al. |
| 2004/0133280 | A1 | 7/2004 | Trieu |
| 2007/0123906 | A1 | 5/2007 | Errico et al. |
| 2007/0123995 | A1 | 5/2007 | Thelen et al. |
| 2009/0254182 | A1* | 10/2009 | Kovarik .................. A61L 27/12 623/17.11 |
| 2012/0071933 | A1 | 3/2012 | DeRidder |
| 2013/0197588 | A1 | 8/2013 | Abdou |
| 2014/0277456 | A1 | 9/2014 | Kirschman |
| 2016/0038309 | A1 | 2/2016 | Doyle |
| 2016/0151171 | A1 | 6/2016 | Mozeleski et al. |
| 2016/0166396 | A1 | 6/2016 | McClintock |
| 2016/0235448 | A1* | 8/2016 | Seex .................... A61B 17/808 |
| 2017/0049579 | A1 | 2/2017 | Quinlan et al. |
| 2018/0055651 | A1 | 3/2018 | Moskowitz et al. |
| 2019/0105180 | A1 | 4/2019 | Adamo et al. |
| 2020/0281736 | A1 | 9/2020 | Milz et al. |
| 2020/0345516 | A1* | 11/2020 | Donaldson ............ A61F 2/4455 |
| 2020/0352739 | A1 | 11/2020 | Ouidja et al. |
| 2021/0369467 | A1 | 12/2021 | Seex |
| 2022/0192841 | A1 | 6/2022 | Blain et al. |
| 2023/0157838 | A1 | 5/2023 | Shin |
| 2023/0165690 | A1 | 6/2023 | Blain et al. |
| 2023/0372122 | A1 | 11/2023 | Martin et al. |
| 2024/0108387 | A1 | 4/2024 | Donald et al. |

FOREIGN PATENT DOCUMENTS

| | | | |
|---|---|---|---|
| EP | 2194898 | B1 | 6/2010 |
| EP | 2618787 | B1 | 7/2013 |
| EP | 2688520 | B1 | 1/2014 |
| EP | 2833842 | A1 | 2/2015 |
| WO | 2005055835 | A2 | 6/2005 |
| WO | 2010036864 | A1 | 4/2010 |
| WO | 2010078488 | A2 | 7/2010 |
| WO | 2023021249 | A1 | 2/2023 |
| WO | 2023023793 | A1 | 3/2023 |
| WO | 2023218263 | A1 | 11/2023 |

OTHER PUBLICATIONS

Spinal Elements, Sapphire X, An MIS Ultra Solution, Copyright Date 2024, 5 Pages.

Zimmer Biomet, MaxAn Anterior Cervical Plate System Surgical Technique Guide, Copyright Date 2017, 36 Pages.

International Search Report, International Application No. PCT/IB2026/053305, File Reference GET-2-PCT, International Filing Date: Apr. 2, 2026, Search Report Mailing Date: Jul. 8, 2026, 5 Pages.

Written Opinion of the International Searching Authority, International Application No. PCT/IB2026/053305, File Reference GET-

(56) References Cited

OTHER PUBLICATIONS

2-PCT, International Filing Date: Apr. 2, 2026, Written Opinion Mailing Date: Jul. 8, 2026, 10 Pages.

* cited by examiner

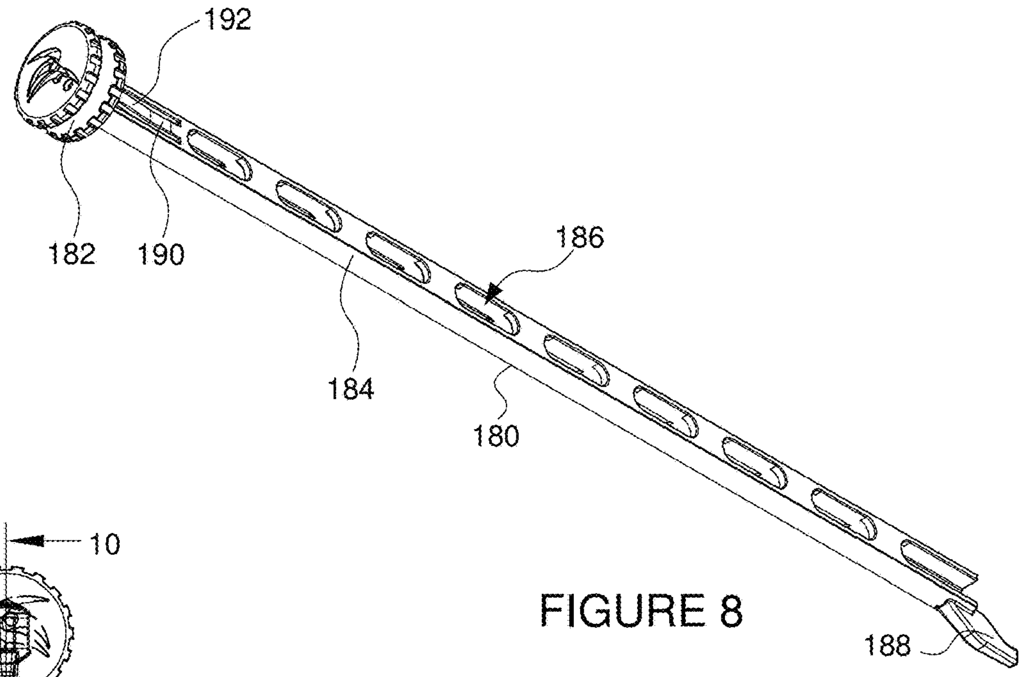
FIGURE 8
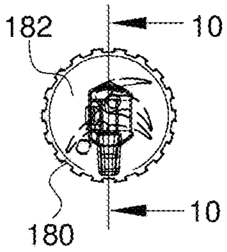
FIGURE 9
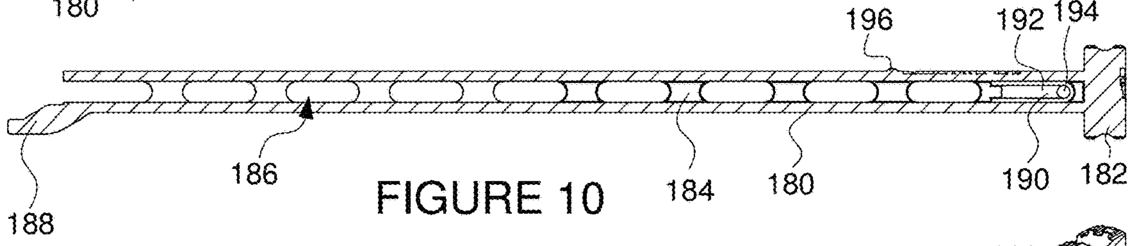
FIGURE 10
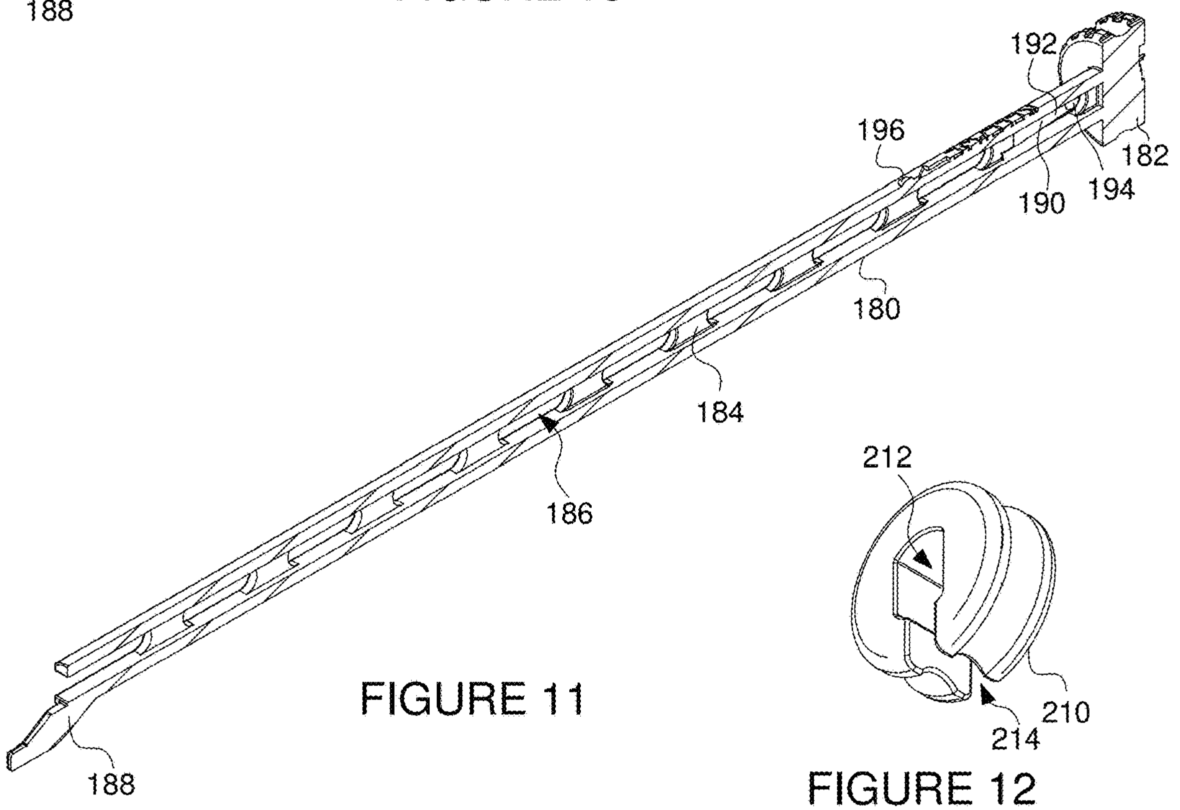
FIGURE 11
FIGURE 12

INTERBODY SPINAL IMPLANTS

FIELD

This disclosure relates to interbody spinal implants.

BACKGROUND

Various surgical techniques have been used to treat spinal conditions. For example, such techniques sometimes involve implanting a spinal interbody spacer such as a cage between adjacent vertebrae, which can result in fusion of the adjacent vertebrae. The interbody spacer can be implanted along with a plate that can be secured to the adjacent vertebrae using fasteners such as screws.

SUMMARY

According to one aspect, a spinal interbody spacer can be positioned using a spinal interbody implant inserter including a spinal interbody implant connector and a depth stop while the interbody implant connector is connected to the interbody spacer and while the depth stop is connected to the interbody implant connector. After positioning the interbody spacer, the depth stop can be removed from a spinal plate path that extends along the interbody implant connector. The spinal plate can slide along the spinal plate path toward the interbody spacer while the interbody spacer is connected to the interbody implant connector and the depth stop is removed from the spinal plate path.

According to another aspect, a spinal interbody implant inserter system can include a spinal interbody spacer and a spinal interbody implant inserter. The interbody implant inserter can include a spinal interbody implant connector that is configured to be removably connected to the interbody spacer and a depth stop that is configured to be removably connected to the interbody implant connector while the interbody implant connector is removably connected to the interbody spacer. The system can also include a spinal plate that is configured to slide along the interbody implant connector toward the interbody spacer while the interbody implant connector is connected to the interbody spacer.

According to yet another aspect, a spinal interbody inserter system can include a spinal interbody spacer and a spinal interbody implant inserter that is configured to be removably connected to the interbody spacer. The system can also include a spinal plate that is configured to slide along a spinal interbody implant connector of the interbody implant inserter toward the interbody spacer while the interbody implant connector is connected to the interbody spacer. The system can also include a plate holder that is configured to hold the spinal plate while the interbody implant inserter is connected to the interbody spacer and the spinal plate is sliding toward the interbody spacer along a central axis that extends along the interbody implant connector. The plate holder can be configured to inhibit rotation of the plate holder around the axis relative to the interbody implant connector and relative to the spinal plate.

According to yet another aspect, a spinal interbody implant connector can be removably connected to a spinal interbody spacer. A spinal plate can slide along the interbody implant connector toward the interbody spacer while the interbody implant connector is connected to the interbody spacer. A plate holder can hold the spinal plate while the interbody implant connector is connected to the interbody spacer and the spinal plate is sliding toward the interbody spacer along a central axis that extends along the interbody implant connector. The plate holder can inhibit rotation of the plate holder around the axis relative to the interbody implant connector and relative to the spinal plate.

According to yet another aspect, a spinal interbody spinal implant inserter system can include a spinal interbody spacer, a spinal interbody implant inserter, and a spinal plate. The interbody implant inserter can include a spinal interbody implant connector that is configured to be removably connected to the interbody spacer. The interbody implant connector can be configured to rotate relative to the interbody spacer from a disconnected position where the interbody implant connector is disconnected from the interbody spacer (although there may be some interaction such as a tip of the interbody implant connector being inserted in a hole of the interbody spacer) to a rotational stop at a set connected position where the interbody implant connector is connected to the interbody spacer. The spinal plate can be configured to slide along the interbody implant connector toward the interbody spacer while the interbody implant connector is connected to the interbody spacer.

According to yet another aspect, a technique can include removably connecting a spinal interbody implant connector to a spinal interbody spacer. The removably connecting can include rotating the interbody implant connector relative to the interbody spacer from a disconnected position to a rotational stop at a set connected position where the interbody implant connector is connected to the interbody spacer.

This Summary is provided to introduce a selection of concepts in a simplified form. The concepts are further described below in the Detailed Description. This Summary is not intended to identify key features or essential features of the claimed subject matter, nor is it intended to be used to limit the scope of the claimed subject matter. Similarly, the invention is not limited to implementations that address the particular techniques, tools, environments, disadvantages, or advantages discussed in the Background, the Detailed Description, or the attached drawings.

BRIEF DESCRIPTION OF THE DRAWINGS

FIG. 8 is a distal facing perspective view of an inserter housing of the interbody implant inserter of FIG. 2.

FIG. 9 is a distal facing view of the inserter housing of FIG. 8.

FIG. 10 is a side sectional view taken along line 10-10 of FIG. 9.

FIG. 11 is a proximal facing perspective view of a section like the side sectional view of FIG. 10.

FIG. 12 is a distal facing perspective view of a lock ring of the inserter housing of FIG. 8.

Figure 1:
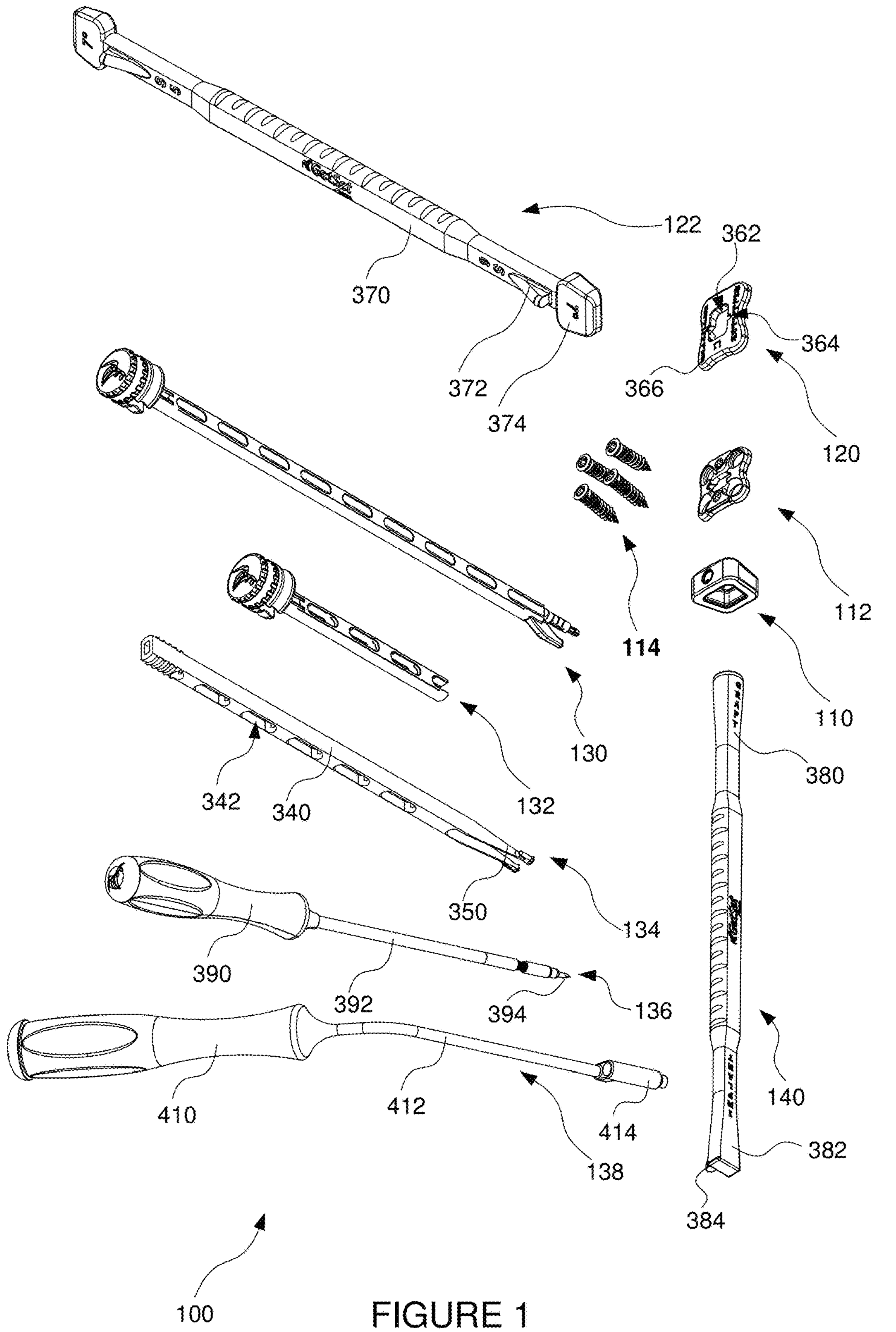
FIG. 1 is a distal facing perspective view of a spinal interbody implant system.
Figure 2:
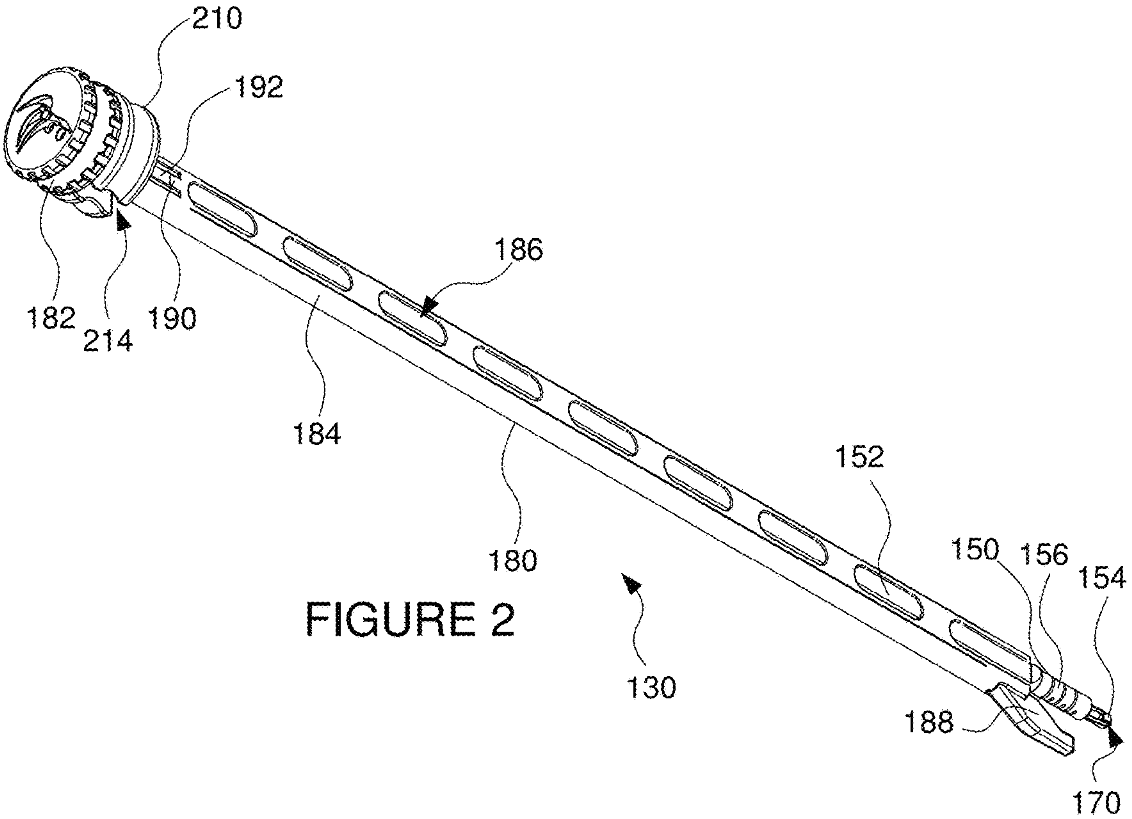
FIG. 2 is a distal facing perspective view of a spinal interbody implant inserter from the system of FIG. 1.
Figure 3:
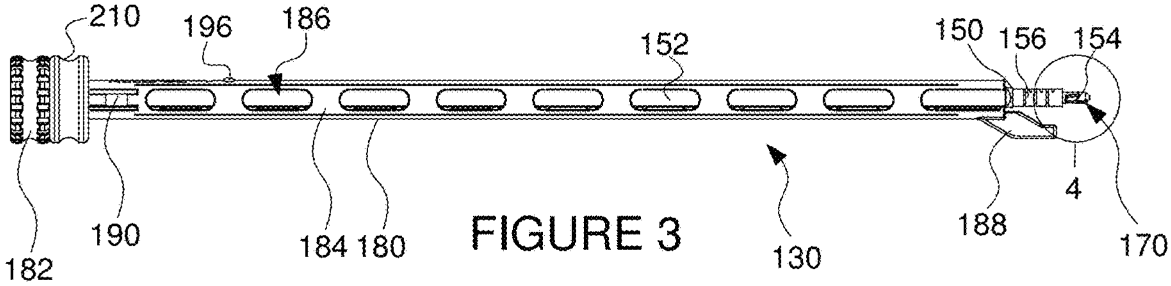
FIG. 3 is a side view of the interbody implant inserter of FIG. 2.

The description and drawings may refer to the same or similar features in different drawings with the same reference numbers. Also, the different components may not be illustrated to scale relative to each other in one or more figures. Some figures illustrate hard tissue spinal bodies such as vertebrae. Those vertebrae are not meant to limit the illustration to any particular vertebrae, and indeed the illustrations of vertebral bodies in the figures illustrate representations of two vertebral bodies that may not be adjacent vertebral bodies in a spine (indeed, the two vertebral bodies are somewhat representative of two cervical vertebrae that would not normally be adjacent to each other in a spine, but they are used herein for convenience to illustrate interbody spinal implant features).

DETAILED DESCRIPTION

Example implementations of the present disclosure may be understood by reference to the drawings. The components of the present disclosure, as generally described and illustrated in the Figures herein, could be arranged and designed in a wide variety of different configurations. Thus, the following more detailed description of the examples of the system and method, as represented in the Figures, is not intended to limit the scope of the present disclosure, as claimed in this or any other application claiming priority to this application, but is merely representative of example implementations of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body. As used herein, the term "proximal," "proximal direction," "proximally" and similar terms generally refer to directions going along the components away from the distal wall of the interbody spacer when in use. As used herein, the terms "distal," "distal direction," "distally" and similar terms generally refer to directions going along the components toward the distal wall of the interbody spacer when in use. The terms of direction discussed herein may be applied to the implants and instruments discussed herein for the sake of simplicity in the description, such as using directional terms with reference to how those implants and instruments may be oriented at least sometimes in use, although the instruments and implants may be oriented in various different ways than described. As just one example of this, the description below will discuss instruments and implants being rotated and/or translated so that their orientation relative to a human body and/or relative to other components may change during procedures. Similarly, they may be oriented in different ways when not used in procedures.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

I. Example Interbody Spinal Implant System

Referring to FIG. 1, a system 100, which can be a spinal interbody spinal implant insertion system, will be discussed. The system 100 may include fewer or more than the components illustrated in FIG. 1. For example, a driver, which is not illustrated, may be utilized in the insertion process such as for driving screws and for rotating stops of a spinal plate to inhibit backout of the screws holding the plate in place. Also, different components may be used in place of those illustrated in FIG. 1, and the components may be configured differently than the examples illustrated in FIG. 1 and the other figures.

The system 100 can include implants such as a spinal interbody spacer 110, which may be a spinal cage; a spinal plate 112; and fasteners such as screws 114 that can be used to secure the spinal plate 112 to spinal bodies such as vertebrae. The implants can also include other components not illustrated in FIG. 1, such as bone graft to be inserted in the interbody spacer 110. The system 100 can also include instruments such as measuring templates and insertion instruments that can be used in inserting the implants. For example, the measuring templates can include a plate template 120 and a spinal interbody spacer template 122.

The insertion instruments can include a spinal interbody implant inserter 130, an extractor 132, and a plate holder 134. The insertion instruments can also include an awl 136 and an awl guide 138, as well as a tamp 140. Examples of components of the system 100 will now be discussed with reference to the drawings.

Referring to FIGS. 1-12, the interbody implant inserter 130 can include a connector 150, which can include a non-circular shaft 152 (such as a shaft with a rectangular cross section) leading to a distal tip 154. A compressible spring 156 can be seated on the shaft 152 adjacent to the distal tip 154. The shaft 152 and the distal tip 154 can be formed as a unitary part, and the spring 156 can be a sleeve having slots formed therein. The spring 156 can be made of a material that is more flexible than material forming the shaft 152 and the distal tip 154. The shaft 152 can define an aperture such as a securing hole 160 therein (see FIG. 7) near a proximal end of the shaft 152.

Figure 4:
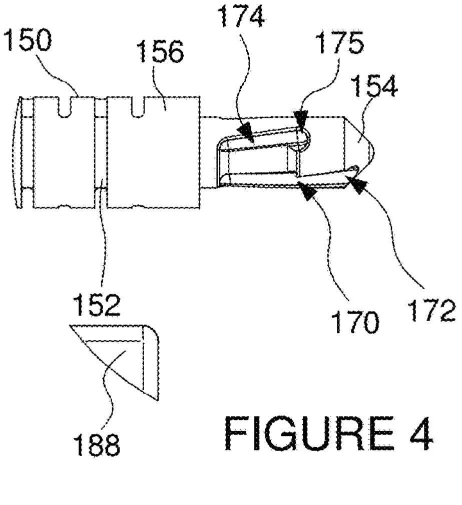
FIG. 4 is an enlarged view cut out along line 4 of FIG. 3.
Figure 5:
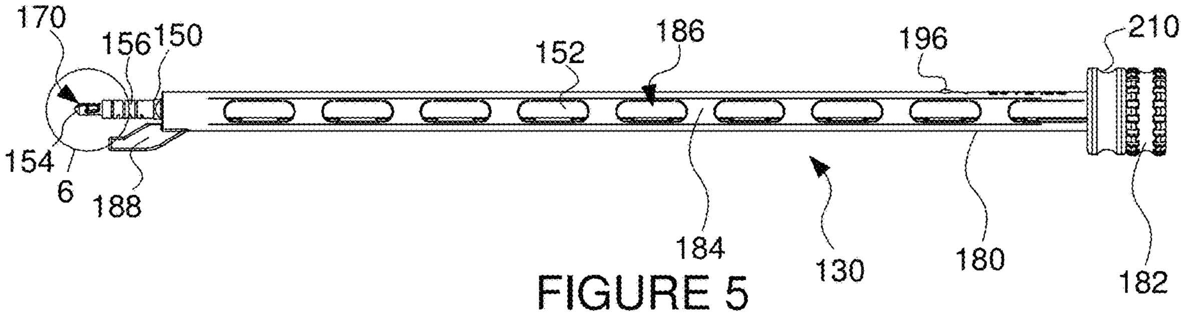
FIG. 5 is a side view opposite the side view of FIG. 3.
Figure 6:
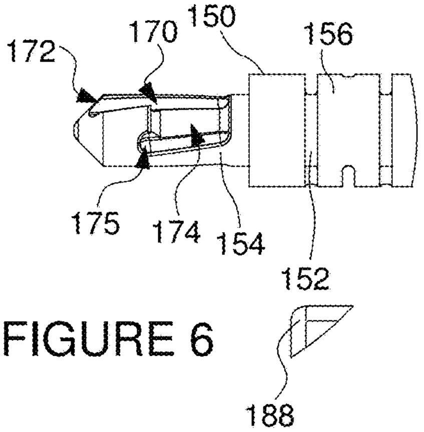
FIG. 6 is an enlarged view cut out along line 6 of FIG. 5.
Figure 7:
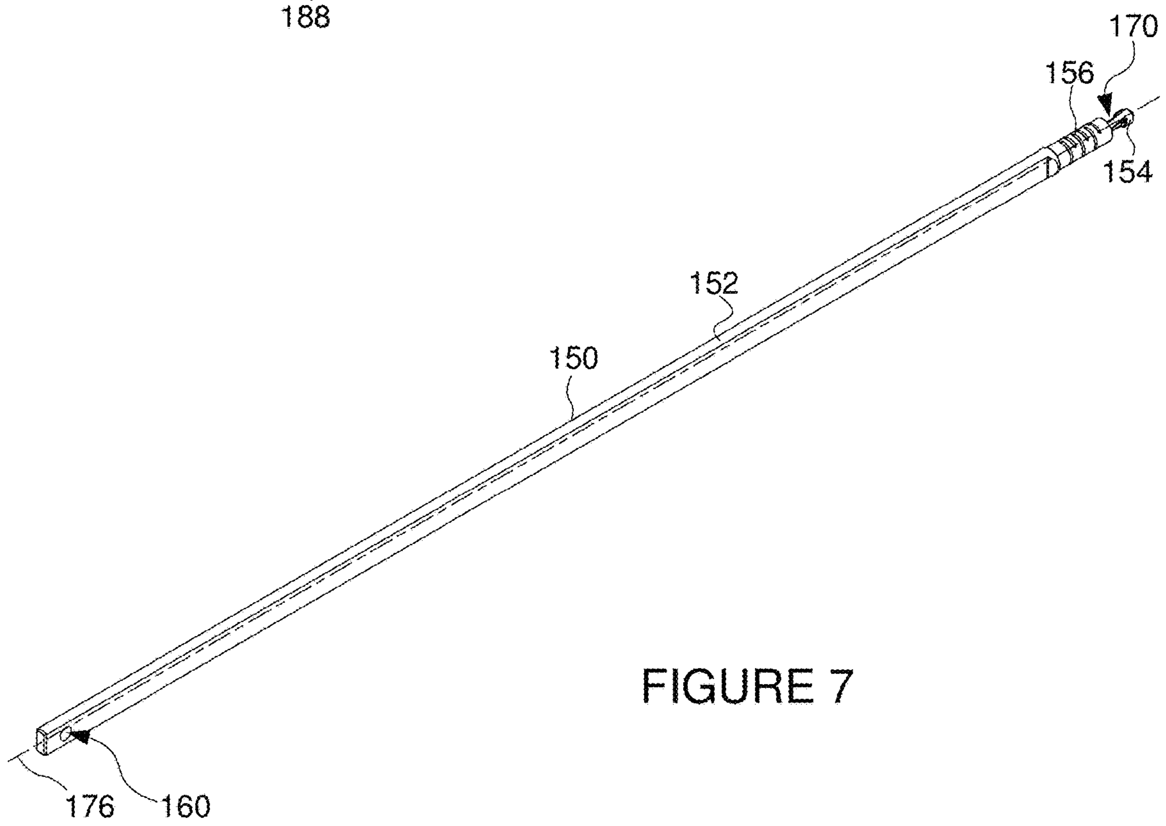
FIG. 7 is a distal facing perspective view of a connector of the interbody implant inserter of FIG. 2.

As illustrated in enlarged views in FIG. 4 and FIG. 6, the distal tip 154 of the connector 150 can define a pair of connecting apertures 170 that can be the same as each other but positioned about one hundred and eighty degrees apart from each other. Each connecting aperture 170 can include a first slot 172 that can extend in a generally proximal direction along the distal tip 154, although the first slot 172 may extend in a somewhat spiral proximal direction. A proximal end of the first slot 172 can open into a second slot 174 that can extend circumferentially around the distal tip 154 from the first slot 172 so that each connecting aperture 170 can be generally L-shaped. The second slot 174 can include a recess 175 that can extend distally from a portion of the second slot 174 that is farthest from the first slot 172 around the distal tip 154. The connector 150 can have a central longitudinal axis 176 (see FIG. 7) extending in a distal-proximal direction along a central portion of the connector 150.

Referring still to FIGS. 1-12, the interbody implant inserter 130 can also include an inserter housing 180. The inserter housing 180 can include a handle 182 at a proximal end of the inserter housing 180. For example, the handle 182 can be a knob. A sleeve 184 can extend distally from the handle 182. The sleeve 184 can define a series of open windows 186 extending through the sleeve and spaced axially along opposite sides of the sleeve 184, with windows 186 on opposite sides of the sleeve 184 being staggered from each other along the distal-proximal directions. Thus, where there is material between adjacent windows 186 on one side of the sleeve 184, a window 186 can be positioned on the other side of the sleeve 184.

The inserter housing 180 can include a depth stop 188. For example, the depth stop can be a finger extending distally from a distal end of the sleeve 184 and transversely away from a central longitudinal axis of the inserter housing 180.

As best seen in FIGS. 10 and 11, the inserter housing 180 can include a latch 190, which can include a cantilever beam 192 and a protrusion 194 at a free end of the cantilever beam. The cantilever beam 192 can generally extend in a proximal direction toward its free end, and the protrusion 194 can extend transversely toward the central longitudinal axis of the inserter housing 180. The cantilever beam 192 can be a spring that can bias the protrusion 194 transversely toward a neutral position.

The inserter housing 180 can also include a lock ring stop 196, which can be a protrusion extending transversely out from the sleeve 184. The lock ring stop 196 can be located distally from the latch 190.

The inserter housing 180 can be removably positioned over the connector 150 with the distal tip 154 of the connector 150 extending distally out of a distal end of the sleeve 184 of the inserter housing, and with a central longitudinal axis of the inserter housing aligning with the central longitudinal axis 176 (see FIG. 7) of the connector 150. The neutral position of the latch 190 can be a position wherein the protrusion 194 is positioned transversely out of engagement with the securing hole 160 in an unlatched position. However, the latch 190 can be pushed transversely inward toward the central longitudinal axis 176 (see FIG. 7) of the connector 150 to push the protrusion 194 of the latch 190 at least partially into the hole 160 in a latched position. In the latched position, the latch 190 can inhibit proximal-distal movement of the inserter housing 180 and the connector 150 away from each other. Also, the sleeve 184 of the inserter housing 180 can have an inner surface forming a non-circular cross section that can match the non-circular cross section of the outer surface of the shaft 152 of the connector 150. Accordingly, the sleeve 184 of the inserter housing 180 and the shaft 152 of the connector 150 can inhibit rotation of the inserter housing 180 and the connector 150 relative to each other when the inserter housing 180 is positioned around the connector 150 (i.e., when the connector 150 is positioned at least partially within the inserter housing 180).

Referring to FIGS. 1-3, 5, and 12, the inserter housing 180 can include a lock ring 210. The lock ring 210 can define a central hole 212 with a cross section that can match a cross section of the outer surface of the sleeve 184. The lock ring 210 can also include a slot 214 that extends transversely out from the central hole 212. The lock ring 210 can be positioned with the central hole 212 receiving the sleeve 184 so that the lock ring 210 can slide between a locked position wherein the lock ring can abut the handle 182 of the inserter housing 180 and an unlocked position wherein the lock ring can abut the lock ring stop 196. In the locked position, the lock ring 210 can push the latch 190 of the inserter housing 180 into the latched position discussed above with the protrusion 194 of the latch 190 entering the securing hole 160 and engaging the connector 150. Thus, with the lock ring 210 in the locked position and the connector 150 seated in the inserter housing 180, the connector 150 and the inserter housing 180 can be secured together, with the interbody implant inserter 130 inhibiting longitudinal or rotational movement of the connector 150 and the inserter housing 180 relative to each other. The lock ring 210 can be slid to the unlocked position (see FIG. 29 discussed below) to unlock the inserter housing 180 and the connector 150 from each other and allow the inserter housing 180 and the connector 150 to slide longitudinally away from each other in the proximal-distal directions.

Figure 13:
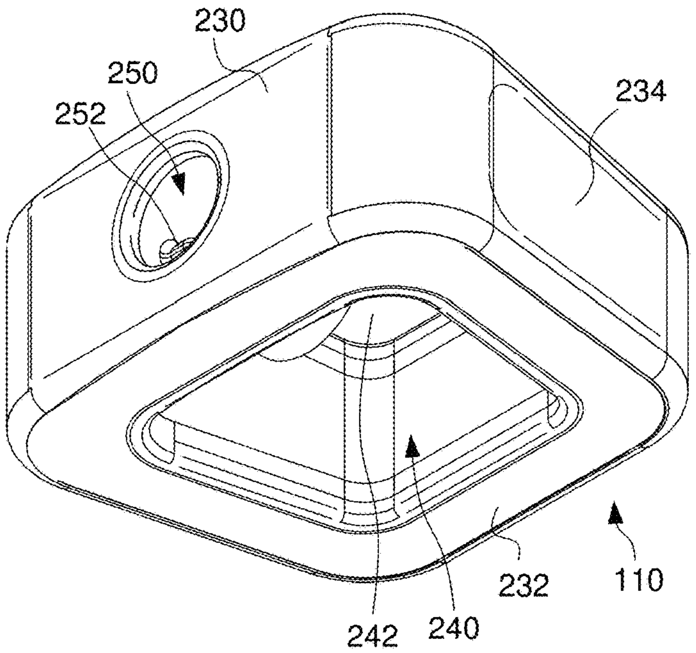
FIG. 13 is a first distal facing perspective view of the interbody spacer of the system of FIG. 1.
Figure 14:
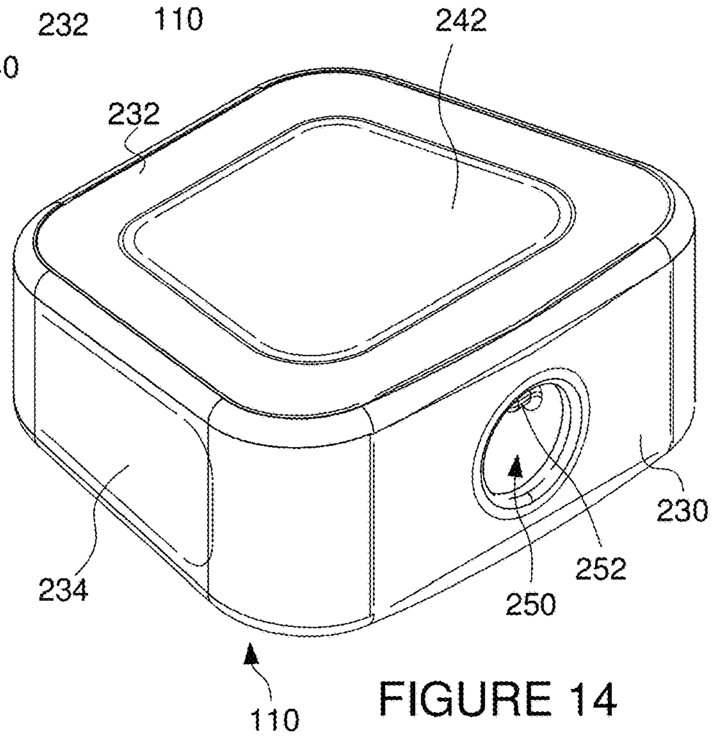
FIG. 14 is a second distal facing perspective view of the interbody spacer of FIG. 13.
Figure 15:
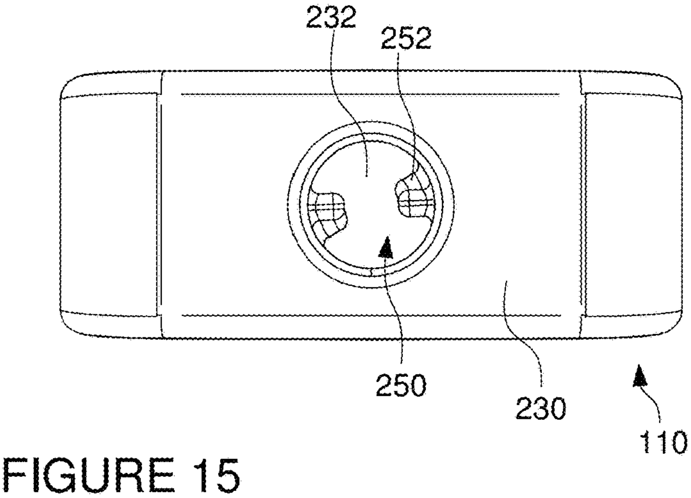
FIG. 15 is a distal facing view of the interbody spacer of FIG. 13.
Figure 16:
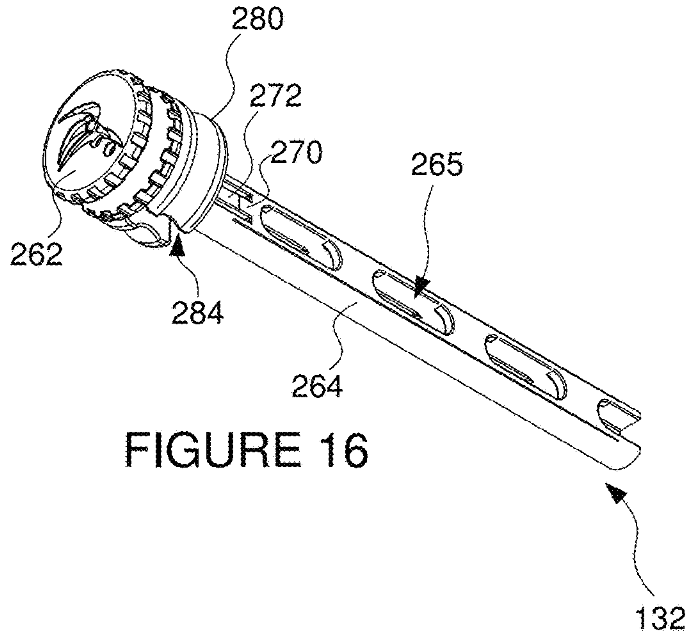
FIG. 16 is a distal facing perspective view of an extractor for extracting a connector of a spinal interbody implant inserter.
Figure 17:
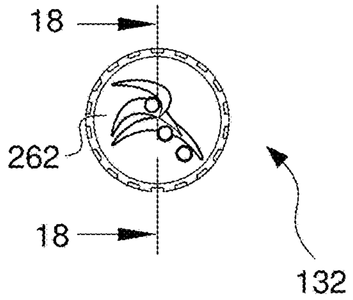
FIG. 17 is a distal facing view of the extractor of FIG. 16.
Figure 18:
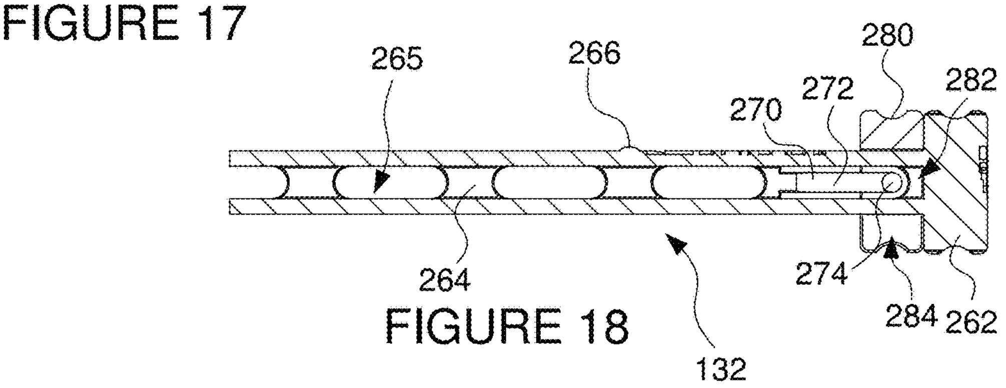
FIG. 18 is a side sectional view taken along line 18-18 of FIG. 17.
Figure 19:
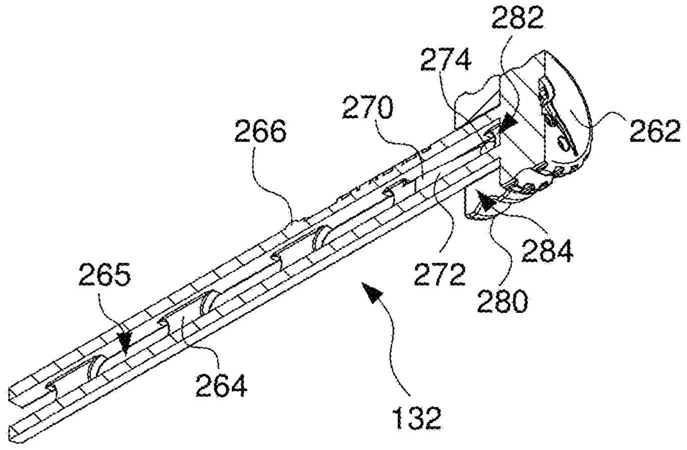
FIG. 19 is a distal facing perspective view of a section like the section illustrated in FIG. 18.
Figure 20:
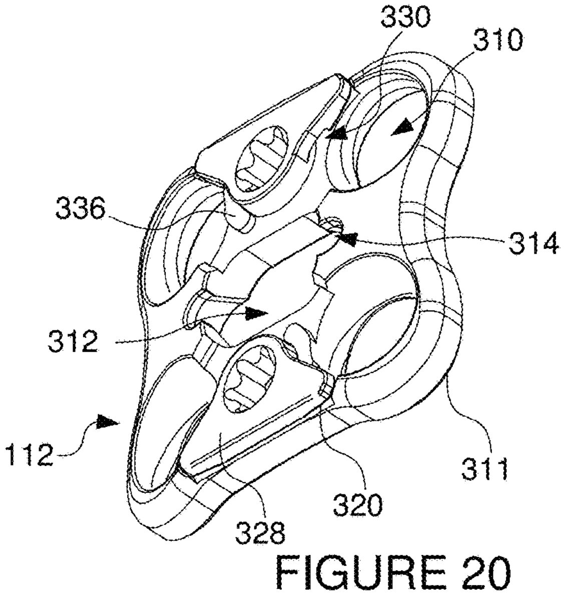
FIG. 20 is a first distal facing perspective view of a spinal plate with stops in unlocked positions.
Figure 21:
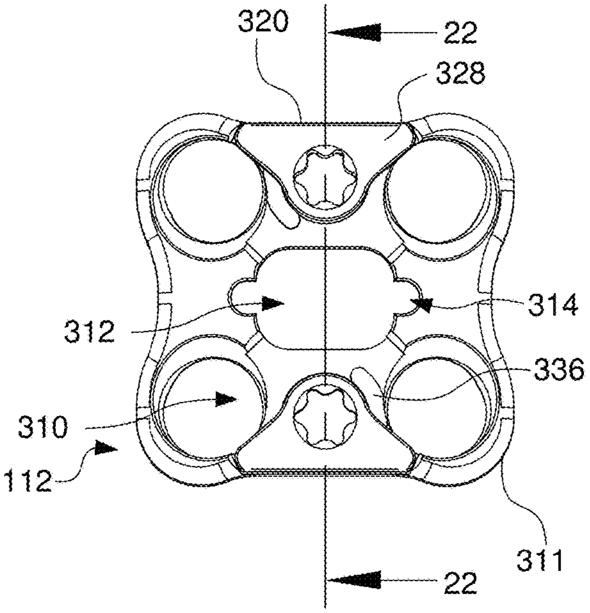
FIG. 21 is a distal facing view of the spinal plate of FIG. 20.
Figure 22:
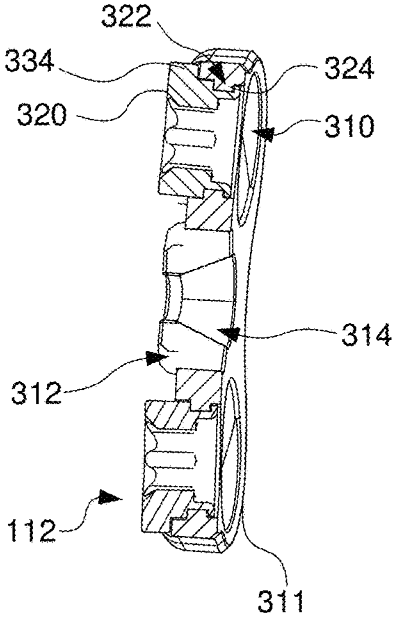
FIG. 22 is a side section view taken along line 22-22 of FIG. 21.

As noted above, the system 100 can also include the interbody spacer 110, which can be a spinal cage. Referring to FIGS. 13-15, the interbody spacer 110 can include a proximal wall 230, a distal wall 232, and a pair of lateral walls 234 joining the proximal wall and the distal wall. The walls are illustrated as being solid in the figures for the sake of simplicity. However, the walls can each include a framework that is joined together for the walls and is filled in with a three-dimensional lattice structure. The interbody spacer 110 can define an interior space 240 between the walls that can receive bone graft material to help promote bone growth after the interbody spacer 110 is implanted. The interbody spacer 110 can also include a closing wall 242, which can extend between the superior or inferior edges of the proximal wall 230, the distal wall 232, and the pair of lateral walls 234 to close off the inferior or superior side of the interior space 240. As with the other walls, the closing wall 242 can be porous to encourage bone growth through the closing wall 242.

The proximal wall 230 can define a connection hole 250 extending from the proximal to distal sides of the proximal wall, into the interior space 240. Connecting protrusions 252 such as ridges can extend radially into the connection hole 250 from opposite sides of the connection hole 250. The connecting protrusions 252 can generally extend axially in, although they may extend in somewhat spiral directions. The connecting protrusions 252 can be configured to extend into the connecting apertures 170 of the distal tip 154 of the connector 150 discussed above. Thus, the distal tip 154 can be inserted into the connection hole 250 with the connecting protrusions 252 sliding along the first slots 172 of the connecting apertures 170. As the connecting protrusions 252 approach the proximal ends of the first slots 172, the spring 156 can push axially against the proximal wall 230 of the interbody spacer 110 and against the connector 150, but additional axial force can be applied to overcome the force of the spring 156. Once the connecting protrusions 252 reach the second slots 174, connector 150 can be rotated less than one hundred and eighty degrees, such as about a quarter turn (about ninety degrees) around its central longitudinal axis 176 (see FIG. 7) relative to the interbody spacer 110 to rotate the connecting protrusions 252 into the second slots 174 until the connecting protrusions 252 reach the recesses 175 at the ends of the second slots 174. The spring 156 can then push the interbody spacer 110 distally relative to the connector 150 to seat distal ends of the connecting protrusions 252 in the recesses 175 of the second slots 174. Thus, the spring 156 can help keep the connecting protrusions 252 seated in connected positions where the distal ends of the connecting protrusions 252 are seated in the recesses 175 of the second slots 174. This can help keep the interbody spacer 110 connected to the connector 150. Also, the contact between the protrusions 252 and the distal tip 154 at the ends of the second slots 174 can form a rotational stop at the connected position that inhibits further rotational movement of the connector 150 relative to the interbody spacer 110. This can provide a set predicted and repeatable rotational connected position of the connector 150 relative to the interbody spacer 110. Because rotation of the spinal plate 112 can be inhibited by the plate holder 134 as discussed herein, this can provide a set predicted and repeatable rotational position of the spinal plate 112 relative to the interbody spacer 110 while the spinal plate 112 is sliding along the connector 150 toward the interbody spacer 110 as discussed herein.

To disconnect the interbody spacer 110 from the connector 150, the connector 150 can be rotated in the opposite direction of the rotation for insertion to move the connecting protrusions 252 out of the recesses 175 and to the second slots 174. The connector 150 can then be pulled in the proximal direction relative to the interbody spacer 110 to move the connecting protrusions 252 along the first slots 172 and to move the distal tip 154 of the connector 150 out of the connection hole 250 of the interbody spacer 110.

Referring now to FIG. 1 and to FIGS. 16-19, the extractor 132 will be discussed. The extractor 132 can be used to disconnect the connector 150 from the interbody spacer 110 and remove the connector 150 from a surgical site. The extractor 132 can be the same as the inserter housing 180 but with a truncated sleeve compared to the inserter housing sleeve and not including a depth stop. Thus, the extractor 132 can include a handle 262, a sleeve 264, windows 265 in the sleeve 264 and a lock ring stop 266 on the sleeve 264, a latch 270 including a cantilever beam 272 and a protrusion 274, and a lock ring 280 defining a central hole 282 and a slot 284. The latch 270 and the lock ring 280 can be used in the same ways and function in the same ways as the latch 190 and the lock ring 210 of the inserter housing 180 discussed above. As with the other components of the system 100, use of the extractor 132 is discussed more below.

Referring now to FIG. 1 and to FIGS. 20-23, the spinal plate 112 will be discussed. The spinal plate 112 can include a main body 311 that defines multiple fastener holes 310, such as four fastener holes 310 in the example illustrated in the figures. However, the spinal plate 112 may include different numbers of fastener holes to receive different numbers of fasteners. The main body 311 can also define a central hole 312, which can be an access hole through which the connector 150 can pass. The central hole 312 can include outwardly extending finger notches 314 on opposite sides of the central hole 312.

Figure 23:
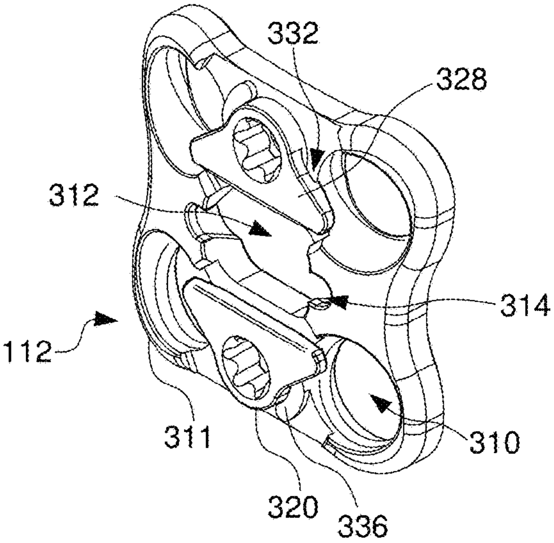
FIG. 23 is a second distal facing perspective view of the spinal plate of FIG. 20 with the stops in locked positions.

The spinal plate 112 can also include stops 320, which can be turned one-half turn between an unlocked position (illustrated in FIGS. 20-22) and a locked position illustrated in FIG. 23. The stops 320 can each include an engaging feature to engage with a driver to allow the driver to turn the stops 320 between the locked and unlocked positions. More specifically, each stop 320 can include a central hub that includes a circumferentially extending groove 322 to receive an inwardly protruding ring 324 of the general plate material to hold the stop 320 in place but allow it to rotate relative to the remainder of the spinal plate 112. Each stop 320 can also include a pair of arms 328 that can rotate to block the adjacent fastener holes 310 in the locked position and to unblock the adjacent fastener holes 310 in the unlocked position. Also, each stop 320 can define a curved lock position channel 330 and a curved unlock position channel 332, with the lock position channel 330 and the unlock position channel 332 being separated by a blocking wall 334. The main body 311 of the spinal plate 112 can include a curved protrusion 336 positioned to fit within the lock position channel 330 and the unlock position channel 332 for each stop 320. Each stop 320 can be rotated relative to the main body 311 until the protrusion 336 extends into the lock position channel 330 and abuts a first side of the blocking wall 334 in the locked position illustrated in FIG. 23 to form a rotational block of the stop 320 due to contact between the first side of the blocking wall 334 and the protrusion 336. Also, each stop 320 can be rotated until the protrusion 336 extends into the unlock position channel 332 and abuts a second side of the blocking wall 334 (which is located opposite the first side of the blocking wall) in the unlocked position illustrated in FIGS. 20-22 to form a rotational block of the stop 320 due to contact between the second side of the blocking wall 334 and the protrusion 336. The rotational bock of the stop 320 in the locked position and in the unlocked position can provide tactile feedback to a user when rotating the stop 320 between the locked position and the unlocked position.

Referring back to FIG. 1, the plate holder 134 will be discussed. The plate holder 134 can include a sleeve 340 similar to the sleeve 184 of the inserter housing 180. The sleeve 340 can include an internal cross section matching an external cross section of the shaft 152 of the connector 150 so that the sleeve 340 can slide along the shaft 152 in distal and proximal directions, but the non-circular cross sections of the shaft 152 and the sleeve 340 can inhibit rotation of the plate holder 134 relative to the connector 150 and therefore relative to a spinal interbody spacer 110 connected to the connector 150. The sleeve 340 can also define windows 342 like the windows of the sleeve 184 of the inserter housing 180.

The plate holder 134 can also include fingers 350 that can be configured as cantilevers so that the fingers 350 can act as springs. The fingers 350 can extend distally from a distal end of the sleeve 340. The fingers 350 can be inserted into the central hole 312 of the spinal plate 112 and the fingers 350 can spring outwardly (away from each other) into the finger notches 314 of the spinal plate 112 to engage the spinal plate 112 and hold the spinal plate 112 relative to the plate holder 134. With the plate holder 134 slid onto the shaft 152 of the connector 150 while holding the spinal plate 112, the fingers 350 can inhibit rotation of the spinal plate 112 around the central longitudinal axis 176 of the connector 150 but can allow some rotation around a different axis (which may be approximately perpendicular to the central longitudinal axis 176) passing through the fingers 350. For example, this can allow some rotation (such as about a ten degree toggle) of the spinal plate 112 around an axis approximately perpendicular to a sagittal plane but inhibit rotation of the spinal plate 112 around an axis approximately perpendicular to a coronal plane relative to the connector 150 and a connected interbody spacer 110 during an implant procedure.

The plate template 120 can generally be shaped similarly to the spinal plate 112. However, the plate template can omit the fastener holes and can be larger than the spinal plate 112. The plate template 120 can include a central hole 362 with outwardly extending finger notches 364 that can be like the finger notches 314 in the spinal plate 112 so that the plate template can be held by the fingers 350 of the plate holder 134. The plate template 120 can also include distance indicators 366 that can indicate distances in the superior and inferior directions from the centrally located finger notches 364. Also, multiple different plate templates and multiple different spinal plates can be included in the system 100 so that an appropriate size of template can be used to judge the corresponding appropriate size of spinal plate 112, and that selected spinal plate 112 can be implanted as discussed herein.

The interbody spacer template 122 can include a handle 370 and a depth stop 372 and imitation interbody spacer 374 on each end of the handle 370. Each imitation interbody spacer 374 can be a different size and/or shape. Also, multiple different interbody spacer templates and multiple different interbody spacers can be included in the system 100 so that an appropriate size of template can be used to judge the corresponding appropriate size of interbody spacer 110, and that selected interbody spacer 110 can be implanted as discussed herein.

The tamp 140 can be a double tamp that can be used to tamp bone graft material in the interbody spacer 110, and possibly to tamp the interbody spacer 110 into position between adjacent vertebral bodies. The tamp 140 can include a graft end 380 and an implant end 382. That graft end 380 can contact the bone graft material to tamp the bone graft material into the interbody spacer 110. The opposite implant end 382 can contact the interbody spacer 110 to tamp the interbody spacer 110 into place relative to the adjacent vertebral bodies. The tamp 140 can include a depth stop 384 at the implant end 382 to inhibit over insertion of a spinal interbody spacer 110 by the tamp 140.

The awl 136 can include a handle 390, a shaft 392 extending in a distal direction from the handle 390, and a tip 394 at a distal end of the shaft 392. A portion of the shaft 392 can be flexible. The awl guide 138 can include a handle 410, a bent shaft 412 extending in a distal direction from the handle 410 and a sleeve 414 at a distal end of the shaft 412. The sleeve 414 can be configured to receive a distal end of the shaft 392 of the awl 136, with the tip 394 of the awl protruding from a distal end of the sleeve 414. The awl guide 138 can be used to guide the tip 394 of the awl 136 as the awl 136 is used to prepare vertebral bodies to receive the screws 114 to secure the spinal plate 112 to the vertebral bodies thereby holding the spinal plate 112 in place and assisting in stabilizing the vertebral bodies relative to each other via the spinal plate 112.

The components of the system 100 discussed herein can be formed of materials that are sufficiently strong, hard, and durable, and that are suitable for use in implants and instruments for use in living bodies. For example, the components may be formed of titanium alloys. However, other alternative materials may be used, such as polymer materials, composite materials, and/or other metals. Also, dimensions of the components may be altered to yield desirable properties, such as desirable strength and flexibility properties. For example, thicknesses in different areas of the components may be altered to provide desired balance of strength and flexibility for different features of the components. Manufacturing techniques for making the components of the system 100 may include standard techniques for making and post-processing parts for surgical implants and instruments, such as molding techniques, additive techniques (such as 3D printing), and/or subtractive techniques (such as milling, drilling, grinding, polishing, etc.). Also, some of the components, such as the interbody spacer 110, the screws 114, the plate template 120, the interbody spacer template 122, the tamp 140, and the plate holder 134 can each be a monolithic part. However, in alternative implementations, one or more of these components may be made of multiple parts that are permanently or temporarily secured together.

The lock ring 210 of the inserter housing 180 and the lock ring 280 of the extractor 132 can be assembled on the respective sleeve 184 and sleeve 264 by sliding the lock ring proximally onto the sleeve from the distal end of the sleeve and forcing the lock ring past the respective lock ring stop 196 or lock ring stop 266. However, the lock rings could be assembled onto the respective sleeves in some other way, such as having the handles of the inserter housing 180 and extractor 132 be secured onto the respective sleeves after the lock rings have been assembled on the sleeves. Similarly, the stops 320 of the spinal plate 112 can be pressed into position in an assembly process, or positioned in some other way.

II. Example Spinal Implant Techniques

Figure 24:
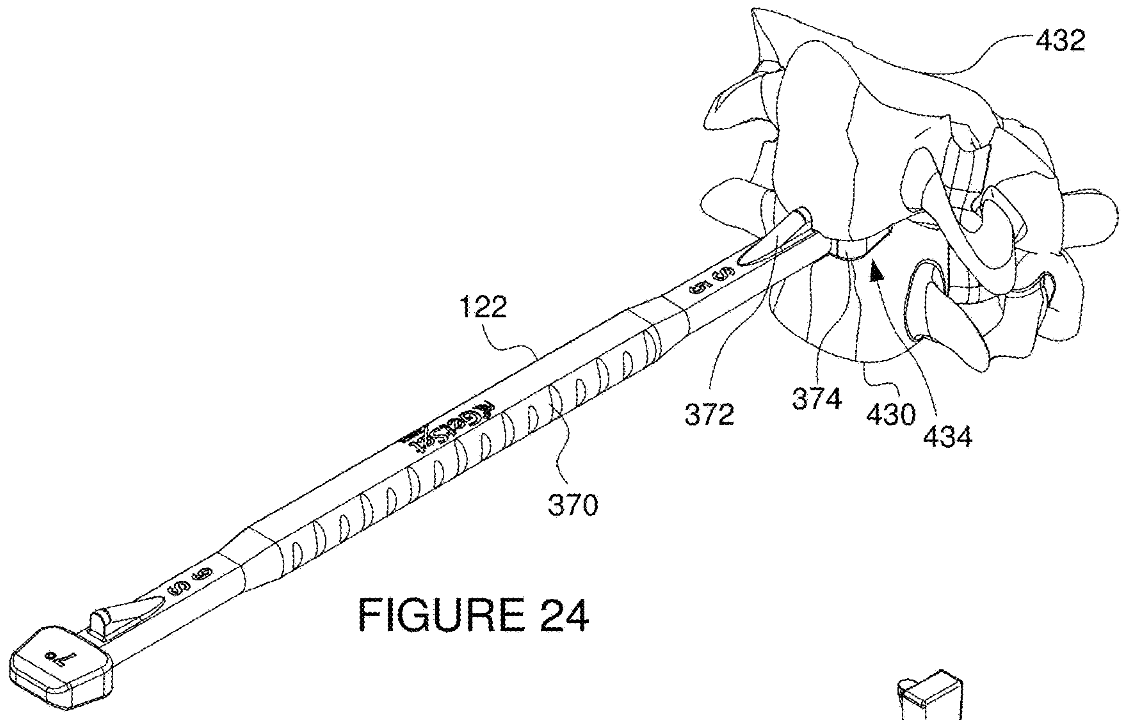
FIG. 24 is a distal facing perspective view of a spinal interbody spacer template in use with an imitation interbody spacer inserted in a spinal interbody space between hard tissue spinal bodies.

An example of using the system 100 for implanting a spinal interbody spacer and plate implant will now be discussed. Referring to FIG. 24, a pair of vertebral bodies are illustrated, including an inferior body 430 and a superior body 432. This section will discuss implanting the interbody spacer 110 and the spinal plate 112 into a spinal interbody space 434 between the superior body 432 and the inferior body 430. A technique can include providing access to and preparing the interbody space 434. This can include creating at least one incision to access the interbody space 434 and removing soft tissue from the interbody space 434 where the interbody spacer 110 is to be inserted.

Once the surgical site is prepared, one or more imitation interbody spacers 374 of one or more interbody spacer templates 122 can be inserted into the interbody space 434, as illustrated in FIG. 24, until a proper fitting imitation interbody spacer 374 is found to fit satisfactorily in the interbody space 434. The corresponding interbody spacer 110 having a size and shape like the satisfactory imitation interbody spacer 374 can then be prepared for insertion into the interbody space 434.

Figure 25:
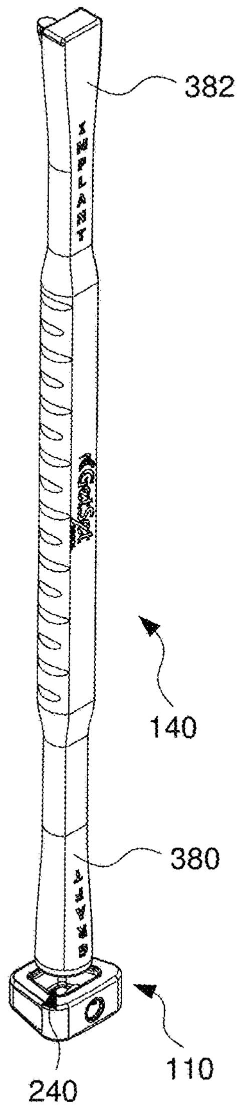
FIG. 25 is a distal facing perspective view of a tamp and a spinal interbody spacer.

For example, preparation of the interbody spacer 110 can include inserting bone graft material (not shown) into the interior space 240 of the interbody spacer 110 and tamping the bone graft material with the tamp 140 as illustrated in FIG. 25. Also, the connector 150 of the assembled interbody implant inserter 130 can be connected to the interbody spacer 110.

If the connector 150 was not already secured to the inserter housing 180, then the lock ring 210 could be slid to its unlocked position adjacent to the lock ring stop 196. The shaft 152 of the connector 150 could then be slid into the sleeve 184 of the inserter housing 180 until the securing hole 160 of the connector 150 aligns with the protrusion 194 of the latch 190 of the inserter housing 180. The lock ring 210 could be slid proximally to the locked position so that the lock ring 210 pushes the latch 190 of the inserter housing 180 into the latched position discussed above. In this latched position, the protrusion 194 of the latch 190 can enter the securing hole 160 and engage the connector 150 to inhibit longitudinal sliding of the connector 150 and the inserter housing 180 relative to each other in the proximal-distal direction.

Figure 26:
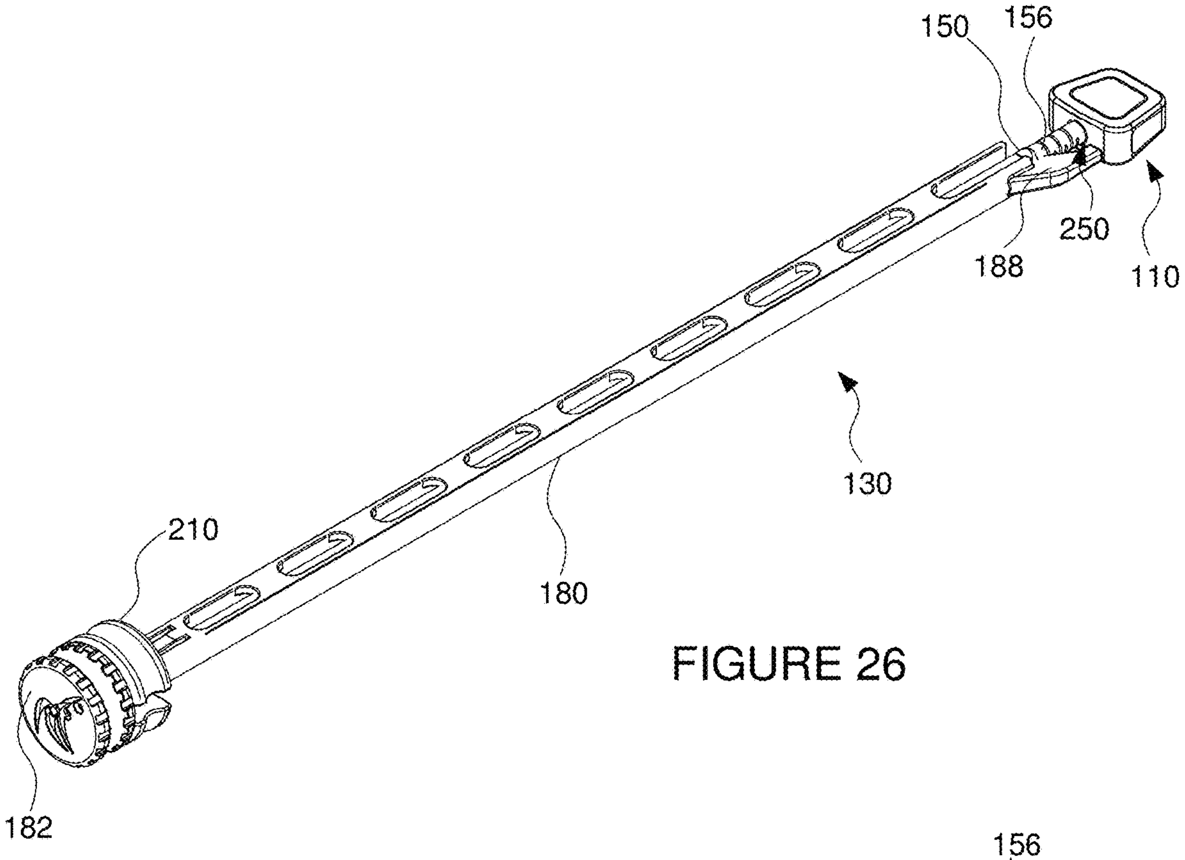
FIG. 26 is a distal facing perspective view of a spinal interbody implant inserter with a tip inserted into a spinal interbody spacer in a disconnected position.
Figure 27:
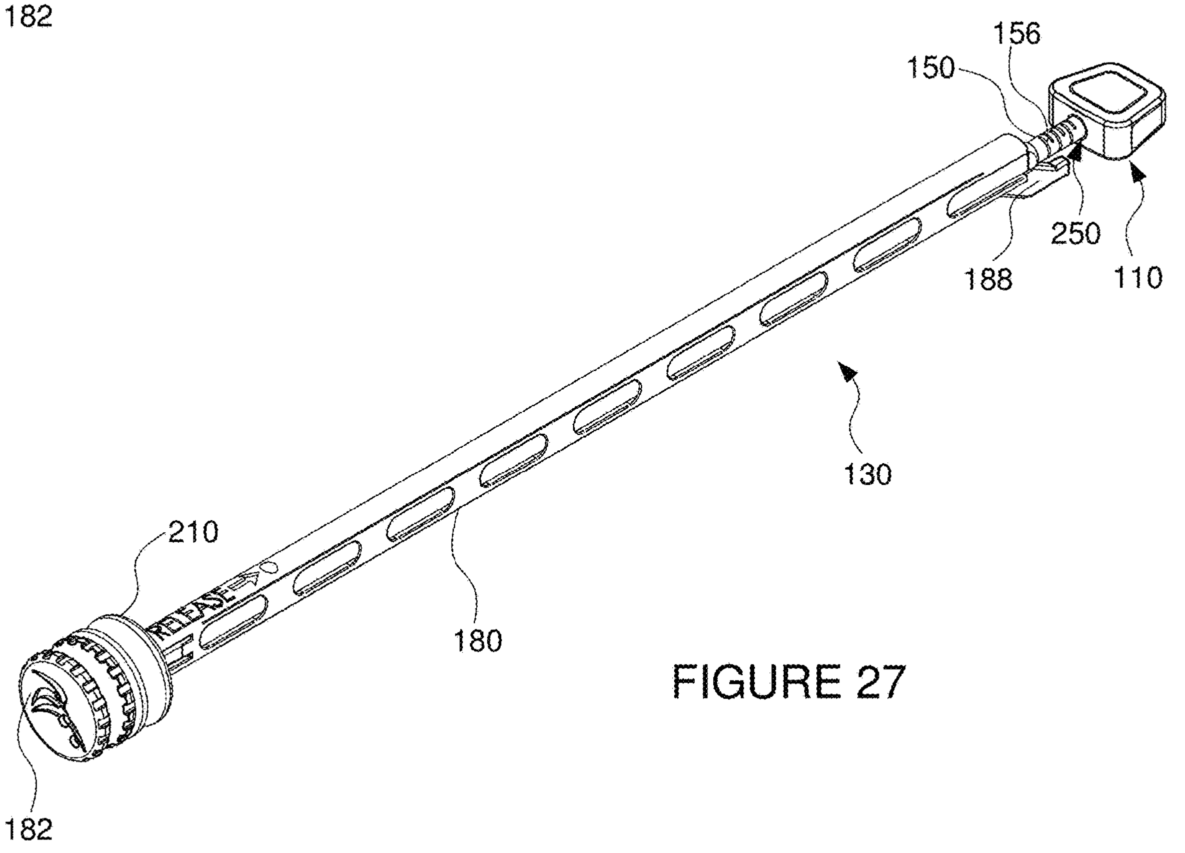
FIG. 27 is a distal facing perspective view like FIG. 26 but with the interbody implant inserter rotated to a connected position.

As illustrated in FIG. 26, with interbody implant inserter 130 assembled with the connector 150 secured to the inserter housing 180, the distal tip 154 of the connector can be inserted into the connection hole 250 of the proximal wall 230 of the interbody spacer 110. This can be done with the protrusions 252 in the connection hole 250 aligned to slide into the first slots 172 of the distal tip 154. With the distal tip 154 fully inserted in the connection hole 250 and the protrusions 252 fully extended into the first slots 172 (in the position illustrated in FIG. 26), the interbody implant inserter 130 can be turned a quarter turn, such as a quarter turn clockwise when facing in the distal direction, to slide the protrusions 252 through the second slots 174 in the distal tip 154 to the recesses 175 (as illustrated in FIG. 27). This can connect the interbody implant inserter 130 and the interbody spacer 110, as discussed more above.

Figure 28:
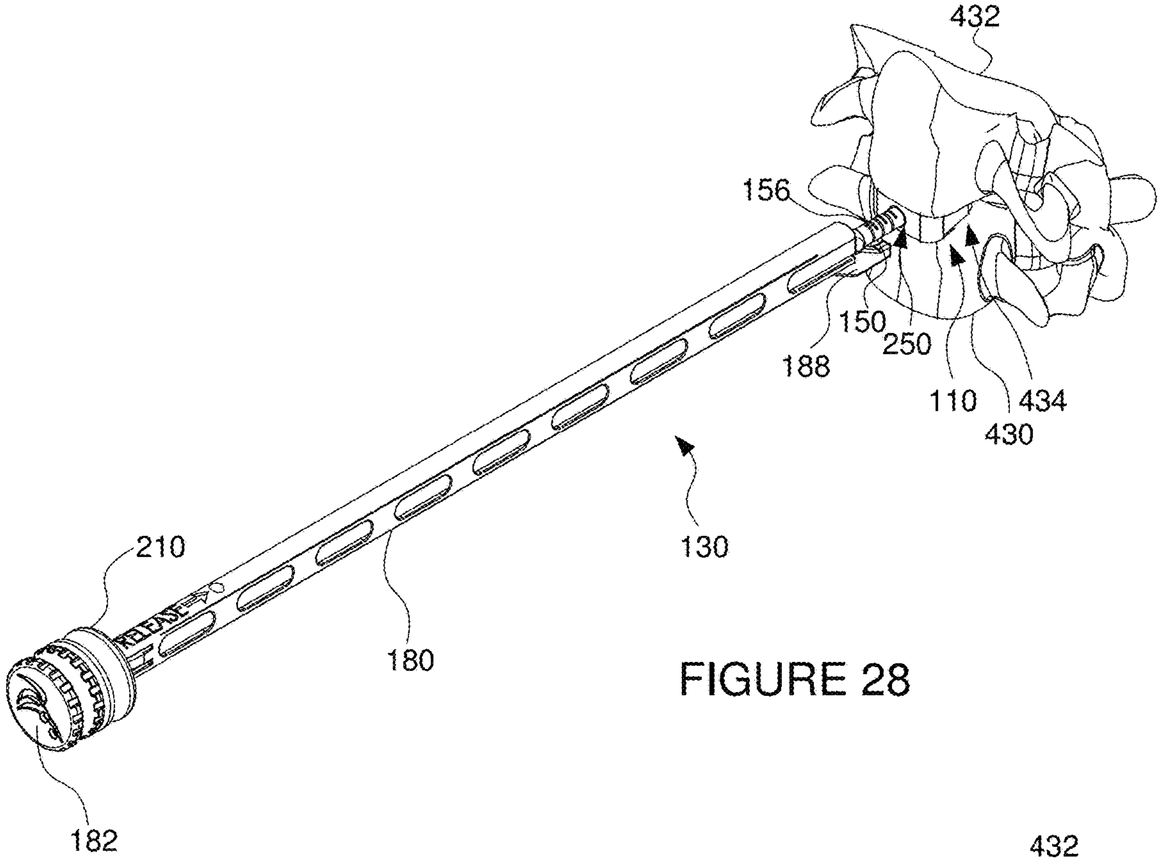
FIG. 28 is a distal facing perspective view like FIG. 27 but with the interbody spacer inserted into the interbody space of between the spinal bodies of FIG. 24.

Referring to FIG. 28, the interbody implant inserter 130 can then be used to insert the interbody spacer 110 into the interbody space 434 until the depth stop 188 contacts the inferior body 430 or the superior body 432 (the inferior body 430 in the illustration of FIG. 28). That contact between the depth stop 188 and the inferior body 430 can inhibit over insertion of the interbody spacer 110 by the interbody implant inserter 130.

Figure 29:
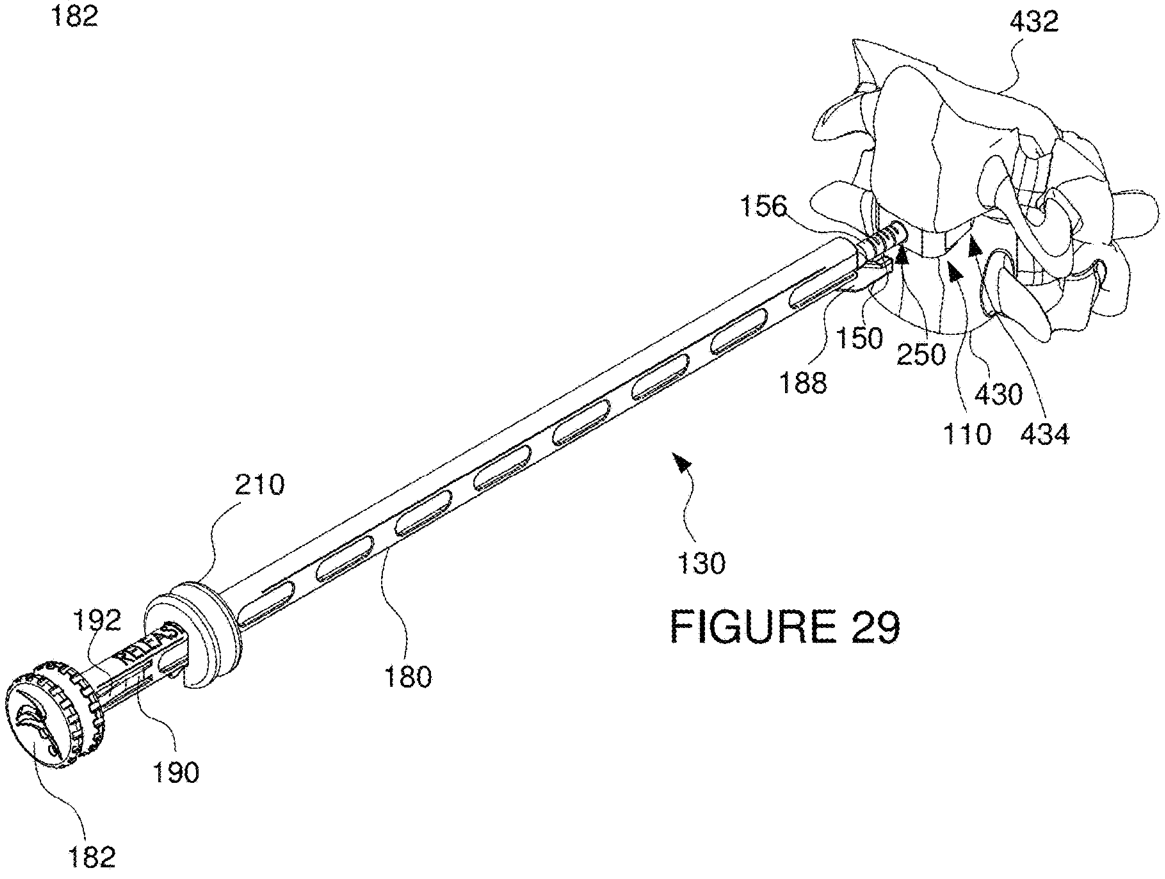
FIG. 29 is a view like FIG. 28 but with a lock ring of an inserter housing of the interbody implant inserter moved from a locked position to an unlocked position.
Figure 30:
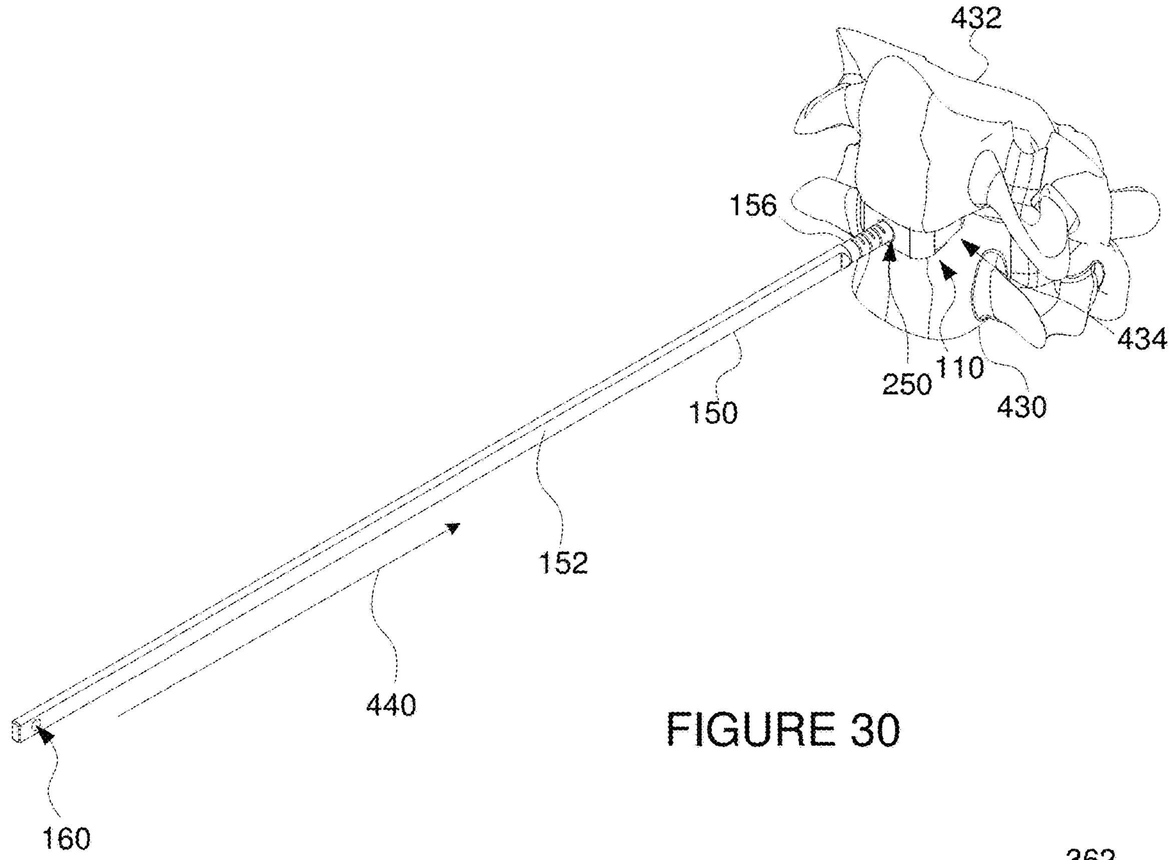
FIG. 30 is a view like FIG. 29 but with the inserter housing removed from a connector of the interbody implant inserter.

While holding the interbody spacer 110 in place, the lock ring 210 of the inserter housing 180 can be slid to its unlocked position, as illustrated in FIG. 29. The inserter housing 180 can then be slid proximally off the connector 150, leaving the connector 150 connected to the interbody spacer 110, as illustrated in FIG. 30. Thus, while the inserter housing 180 including the depth stop 188 can initially be in a spinal plate path 440 to be taken by the spinal plate 112 along the shaft 392 of the connector 150 toward the spinal plate's implant position illustrated in FIGS. 34-40, the inserter housing 180 including depth stop 188 can be removed from the spinal plate path 440. Thus, the inserter housing 180 including the depth stop 188 can be used for proper insertion of the interbody spacer 110 but then removed to cease blocking the movement of the spinal plate 112 along the spinal plate path 440, as discussed below. Thus, a component is in the spinal plate path 440 if the component is positioned to block movement of the spinal plate 112 along the spinal plate path 440 to the spinal plate's implanted position. Likewise, a component is removed from the spinal plate path if the component is no longer positioned to block movement of the spinal plate 112 along the spinal plate path 440.

Figure 31:
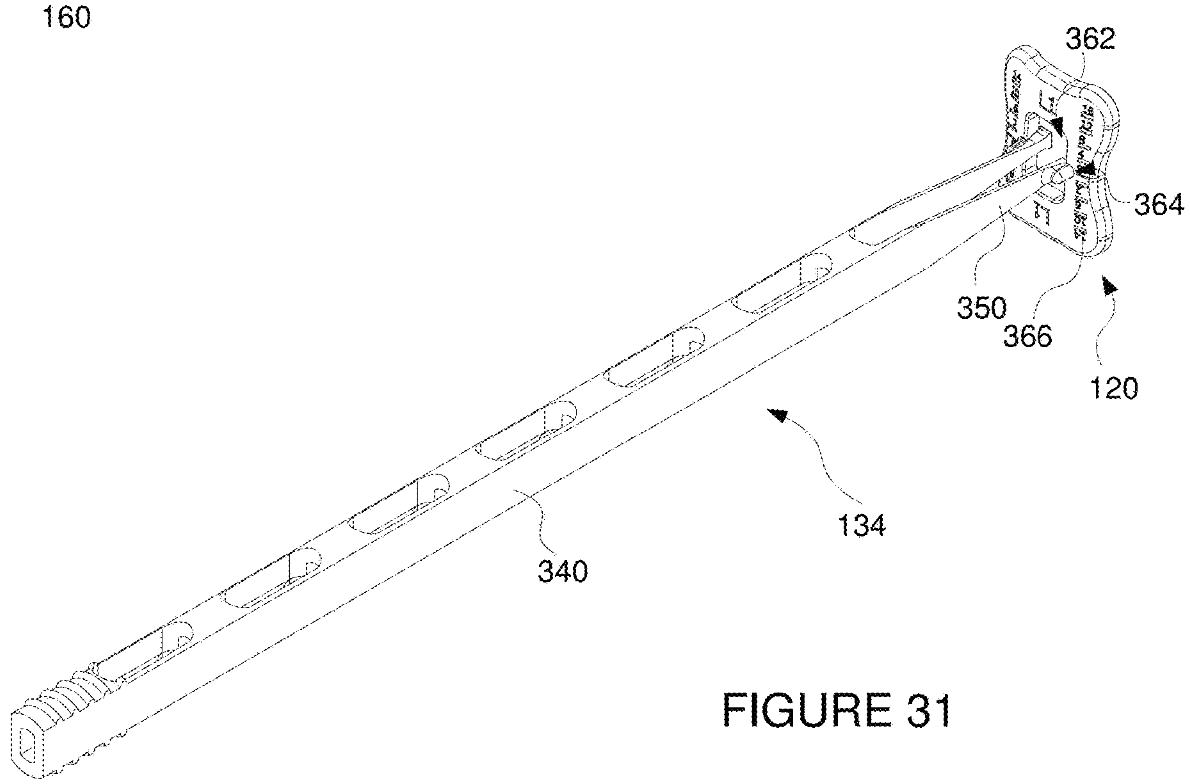
FIG. 31 is a distal facing perspective view of a plate holder holding a plate template.
Figure 32:
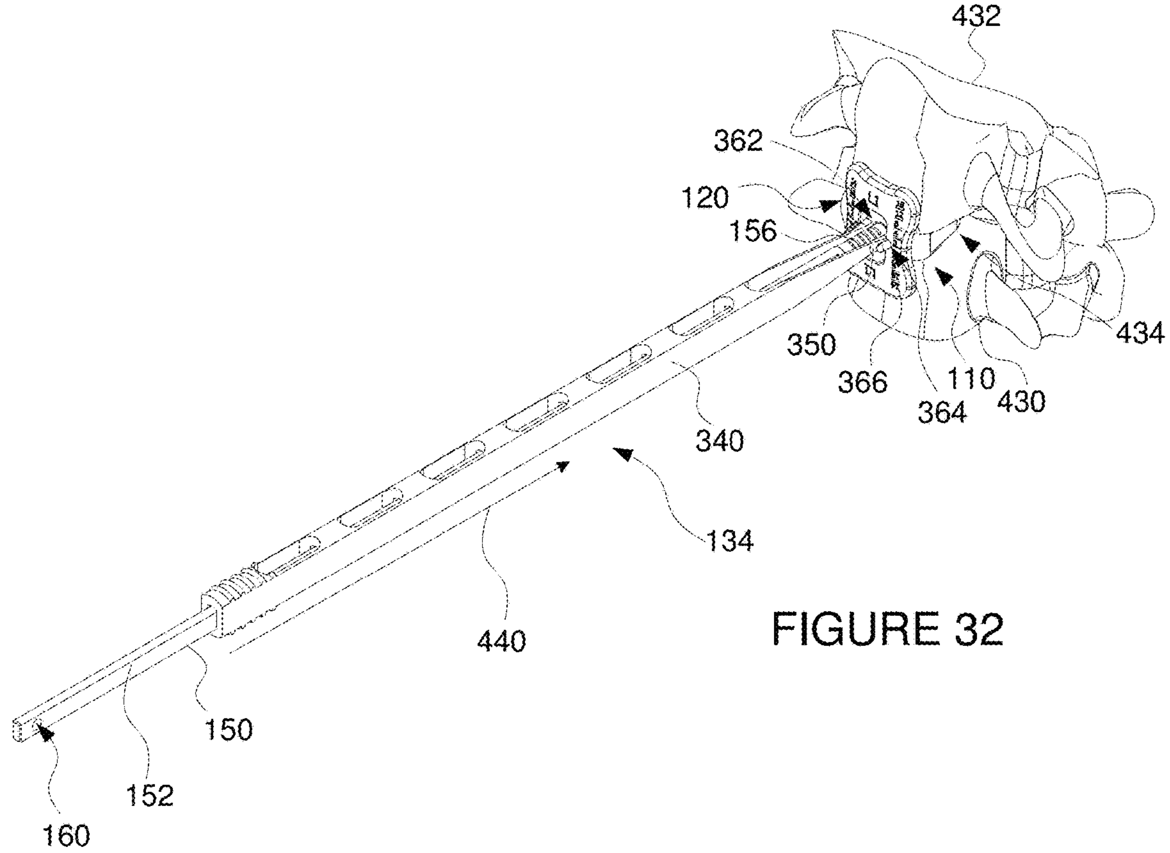
FIG. 32 is a view like FIG. 30 but with a plate holder holding a plate template against the spinal bodies.
Figure 33:
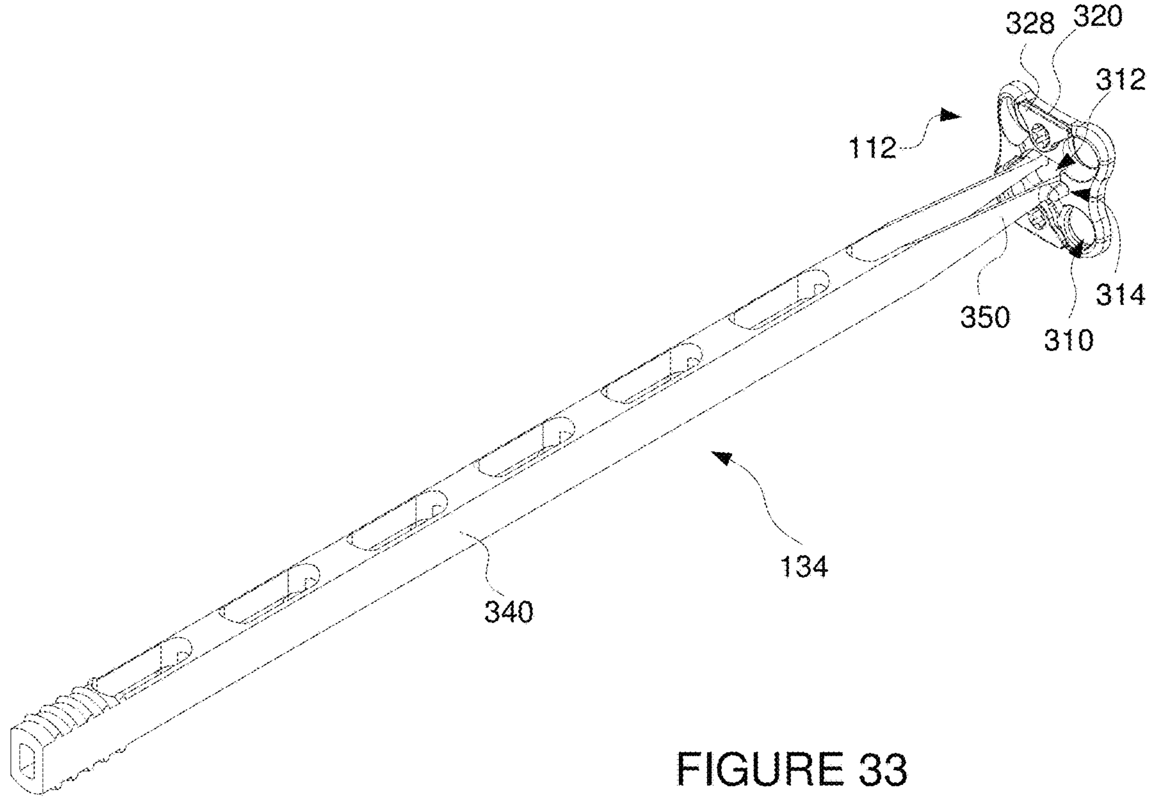
FIG. 33 is a distal facing perspective view of a plate holder holding a spinal plate.

Referring to FIG. 31, the plate holder 134 can then be used to hold the plate template 120 with the fingers 350 of the plate holder 134 being biased outwardly into the finger notches 364 of the plate template 120. Specifically, as an example, the plate holder 134 can be moved in a distal direction until the tips of its fingers 350 extend into the finger notches 364 of the plate template. The fingers 350 may be squeezed to aid in the insertion of the tips of the fingers 350 extending into the finger notches 364 (i.e., at least partially into the finger notches). With the fingers 350 thus positioned in the finger notches 364, the fingers 350 can act as cantilever springs to provide opposing outward biasing forces with the fingers 350 being biased away from each other to press the fingers 350 against the plate template 120 and hold the plate template 120 with the plate holder 134. In an alternative example, the plate holder may include fingers that engage opposite outer edges of the plate template 120 with the fingers squeezing inwardly toward each other to hold the plate template 120. In either example, the fingers can press against the plate template 120 in a transverse direction that is substantially perpendicular to a longitudinal axis of the plate holder 134 and substantially perpendicular to the distal direction in which the plate holder is moved to bring the fingers into engagement with the plate template 120. Referring to FIG. 32, the plate holder 134 can be used to slide the plate template 120 distally along the connector 150 (wherein the path of the plate template 120 can be along the spinal plate path 440) with the shaft 152 sliding through the central hole 362 of the plate template 120 and through the sleeve 340 of the plate holder 134. The plate holder 134 can be used to continue to slide the plate template 120 until the plate template 120 contacts the inferior body 430 and the superior body 432. At this point, the plate template 120 will be centered at about the same position as the spinal plate 112 will be centered when it is secured to the inferior body 430 and the superior body 432. Additionally, the plate holder 134 can engage the shaft 412 of the connector 150 (due to the matching non-circular cross sections of the inner surface of the plate holder 134 and the outer surface of the shaft 412 of the connector 150) to inhibit rotation of the plate holder 134 relative to the connector 150 around the central longitudinal axis 176 (see FIG. 7) of the connector 150. Also, the plate holder 134 can engage the plate template 120 with the engagement of the fingers 350 of the plate holder and the finger notches 364 of the plate template 120 inhibiting rotation of the plate template 120 relative to the plate holder 134 around the central longitudinal axis 176 (see FIG. 7) of the connector 150 (which is aligned with central axes of the plate holder 134 and the plate template 120). However, the plate holder 134 can allow the plate template 120 to rotate (toggle) around an axis that is approximately perpendicular to a sagittal plane, which can allow the tilt of the plate template 120 to match the tilt of the inferior body 430 and the superior body 432. Accordingly, in this position illustrated in FIG. 32, the plate template 120 can be used to determine the appropriate size of spinal plate to be implanted. That spinal plate 112 can then be selected. The plate holder 134 can be slid proximally along the connector 150 to remove the plate holder 134 and the plate template 120 from the surgical site.

Figure 34:
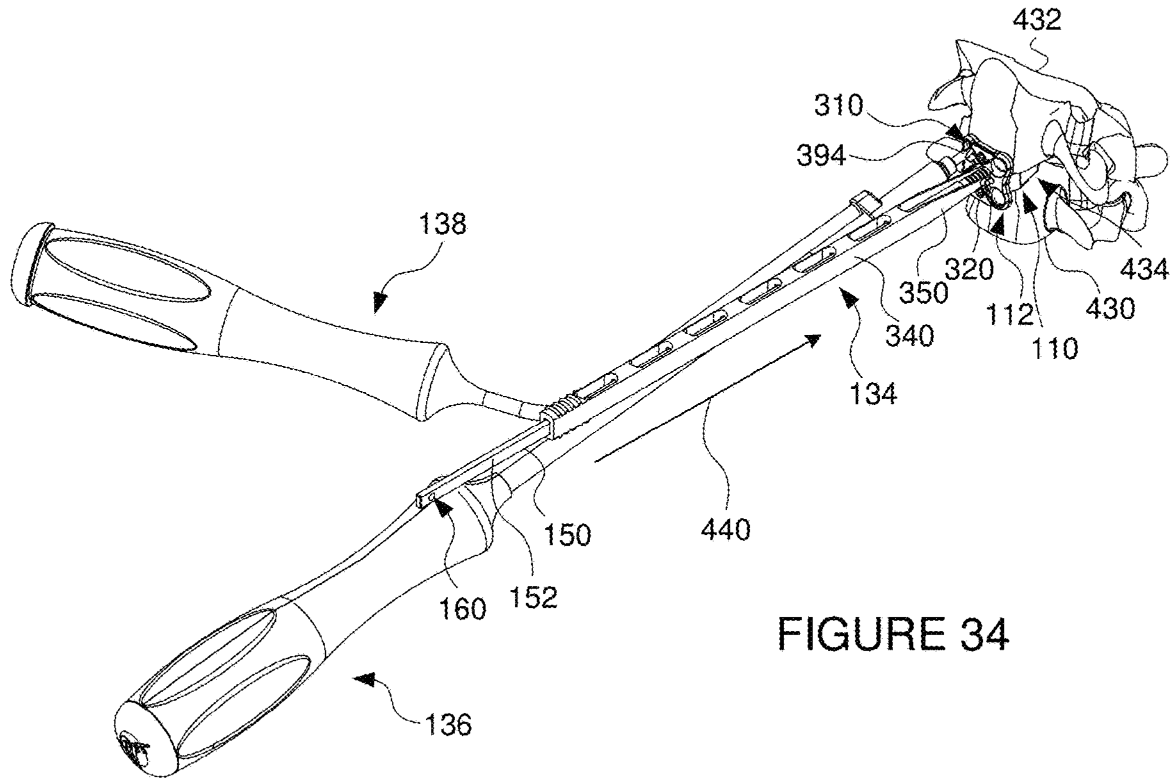
FIG. 34 is a view like FIG. 32 but with the plate template removed and with the plate holder holding a spinal plate, and with an awl and awl guide positioned for preparing holes for screws to be inserted to secure the spinal plate to the spinal bodies.

The plate holder 134 can be connected to hold the spinal plate 112 that has been selected for implanting with the fingers 350 of the plate holder 134 being positioned in the finger notches 314 with the fingers being biased away from each other to engage the spinal plate 112. Specifically, as an example, the plate holder 134 can be moved in a distal direction until the tips of its fingers 350 extend into the finger notches 314 of the spinal plate 112. The fingers 350 may be squeezed to aid in the insertion of the tips of the fingers 350 extending into the finger notches 314. With the fingers 350 thus positioned in the finger notches 314, the fingers 350 can act as cantilever springs to provide opposing outward biasing forces with the fingers 350 being biased away from each other to press the fingers 350 against the spinal plate 112 and hold the spinal plate 112 with the plate holder 134. In an alternative example, a plate holder may include fingers that engage opposite outer edges of the spinal plate 112 with the fingers squeezing inwardly toward each other to hold the spinal plate 112. In either example, the fingers can press against the spinal plate 112 in a transverse direction that is substantially perpendicular to a longitudinal axis of the plate holder 134 and substantially perpendicular to the distal direction in which the plate holder is moved to bring the fingers into engagement with the plate template 120. The plate holder 134 can be used to slide the spinal plate 112 distally along the connector 150 with the shaft 152 sliding through the central hole 312 of the spinal plate 112 and through the sleeve 340 of the plate holder 134. The plate holder 134 can be used to continue to slide the spinal plate 112 along the spinal plate path 440 until the spinal plate 112 contacts the inferior body 430 and the superior body 432, as illustrated in FIG. 34. As discussed above, the spinal plate path 440 is no longer blocked by the inserter housing 180 including the depth stop 188 because the inserter housing has been removed.

At this point, the spinal plate 112 can be centered at about the same position as the plate template 120 was centered when it was used to measure the inferior body 430 and the superior body 432 for selection of the spinal plate 112. The spinal plate 112 can also be generally centered in the superior and inferior directions relative to the interbody space 434 (as was the interbody spacer template 122 in the position illustrated in FIG. 32). Additionally, the plate holder 134 can engage the shaft 412 of the connector 150 (due to the matching non-circular cross sections of the inner surface of the plate holder 134 and the outer surface of the shaft 412 of the connector 150) to inhibit rotation of the plate holder 134 relative to the connector 150 around the central longitudinal axis 176 (see FIG. 7) of the connector 150. Also, the plate holder 134 can engage the spinal plate 112 with the engagement of the fingers 350 of the plate holder and the finger notches 314 of the spinal plate 112 inhibiting rotation of the spinal plate relative to the plate holder 134 around the central longitudinal axis 176 (see FIG. 7) of the connector 150 (which is aligned with central axes of the plate holder 134 and the plate template 120). However, the plate holder 134 can allow the spinal plate 112 to rotate (toggle) around an axis that is approximately perpendicular to a sagittal plane (and approximately perpendicular to the central longitudinal axis 176 (see FIG. 7) of the connector 150), which can allow the tilt of the spinal plate 112 to match the tilt of the inferior body 430 and the superior body 432. Accordingly, in this position illustrated in FIG. 34, the spinal plate 112 is in position to be secured to the inferior body 430 and the superior body 432.

Figure 35:
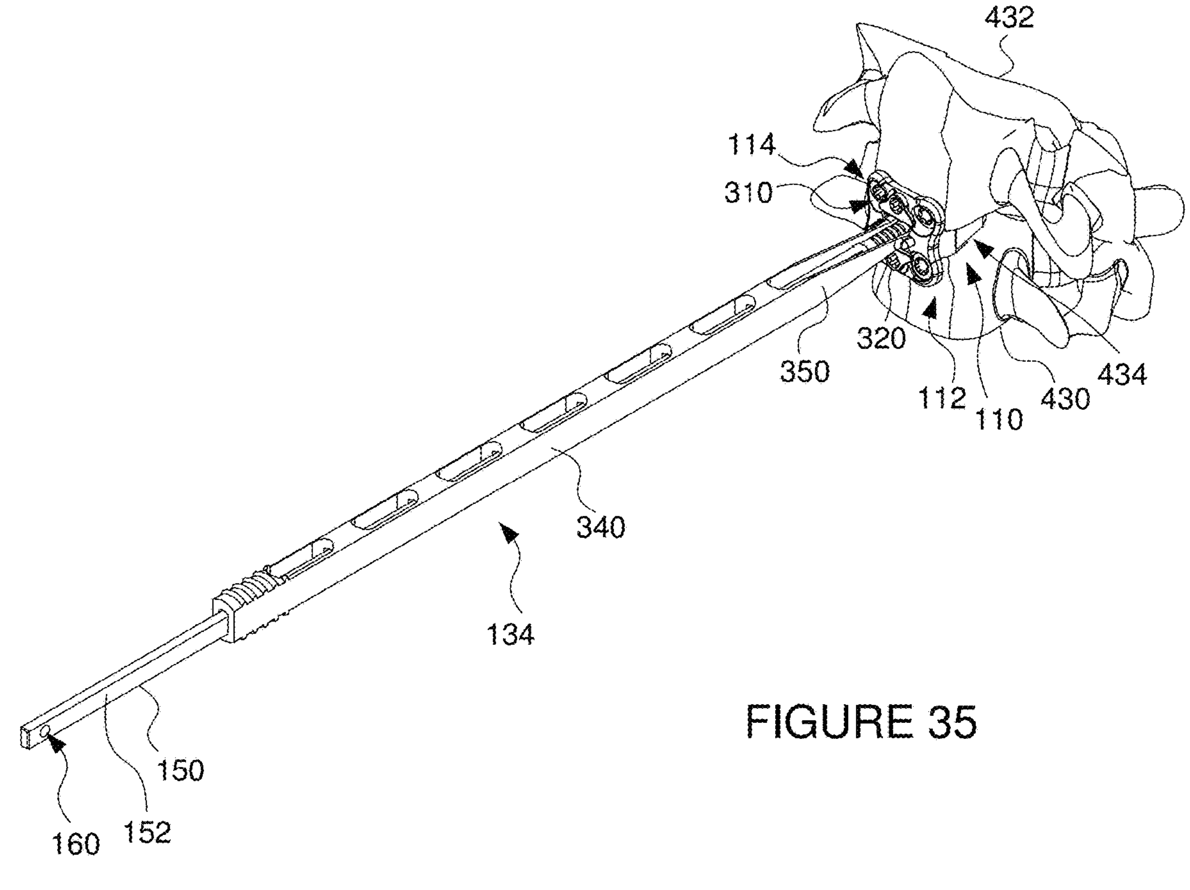
FIG. 35 is a view like FIG. 34 but without the awl and awl guide, and with screws inserted to secure the spinal plate to the spinal bodies, and with stops of the spinal plate rotated from their unlocked positions in FIG. 34 to locked positions.

Accordingly, the spinal plate itself 112 can be used as a template for using the awl 136 as guided by the awl guide 138 to insert the tip 394 through the fastener holes 310 of the spinal plate 112 to prepare holes in the superior body 432 and the inferior body 430 to receive the screws 114. A driver (not shown) can then be used to drive the screws 114 through the fastener holes 310 of the spinal plate 112 and into the prepared holes in the superior body 432 and the inferior body 430. The stops 320 can then be turned to the locked position as illustrated in FIG. 35 (see also FIG. 23) to block the screws 114 from backing out of the holes in the superior body 432 and the inferior body 430. Accordingly, the spinal plate 112 can be secured to the superior body 432 and the inferior body 430, with the interbody spacer 110 positioned in the interbody space 434 between the superior body 432 and the inferior body 430 without the interbody spacer being fixed or directly connected to the spinal plate 112.

Figure 36:
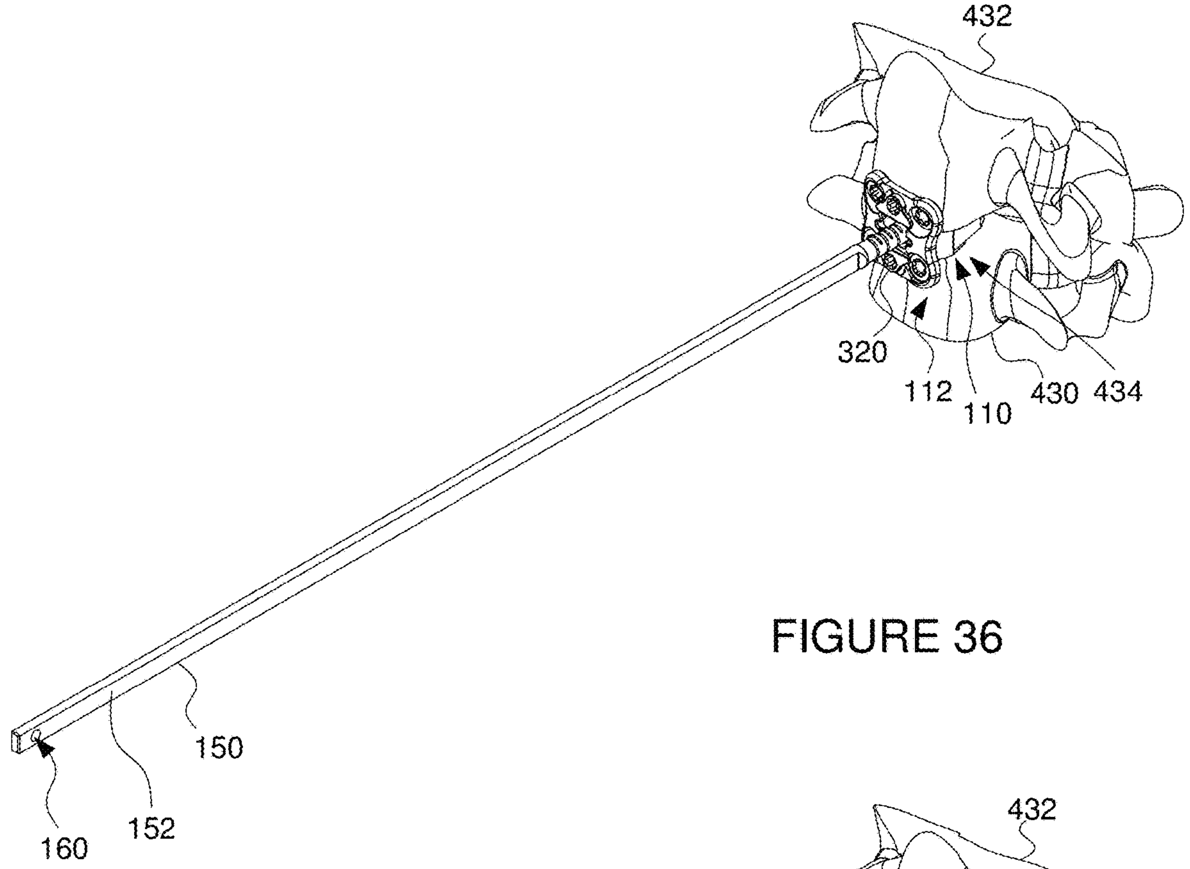
FIG. 36 is a view like FIG. 35 but with the plate holder removed.
Figure 37:
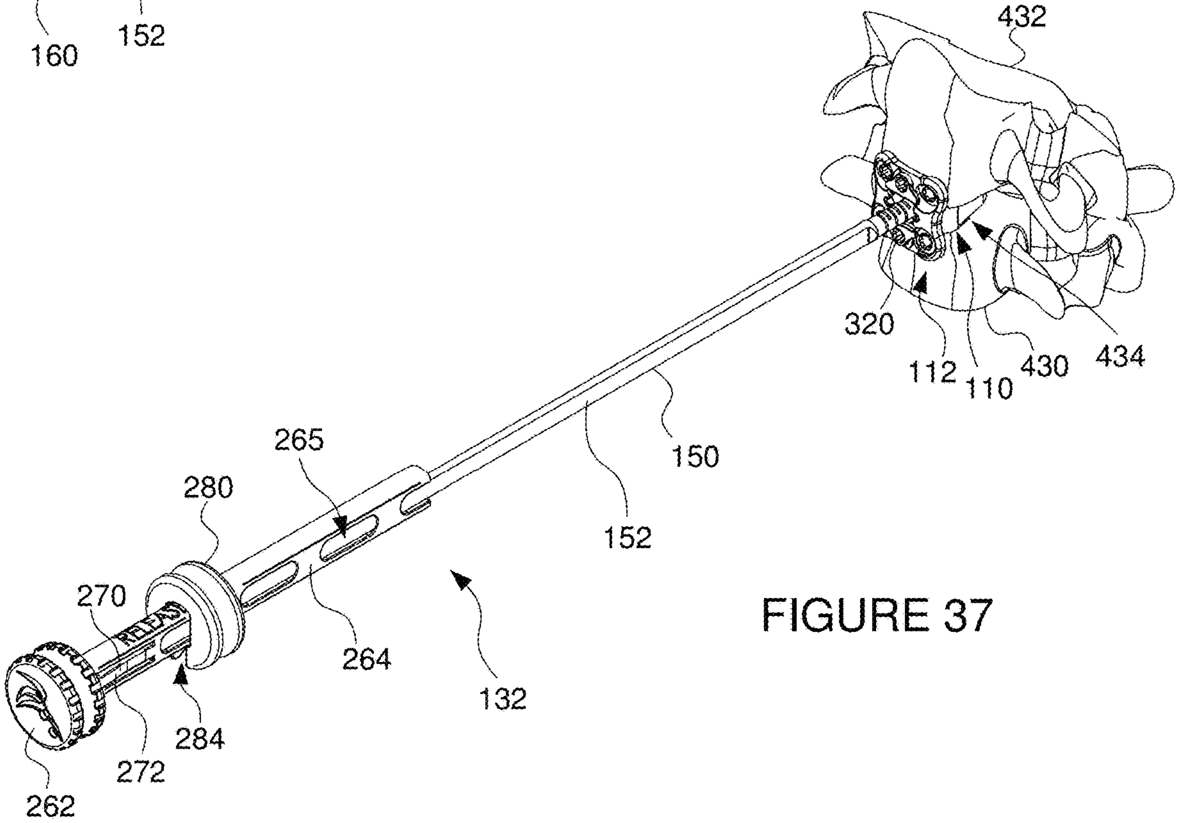
FIG. 37 is a view like FIG. 36 but with an extractor seated on the connector of the interbody implant inserter, and with a lock ring of the extractor in an unlocked position.

The instruments can then be removed from the surgical site. The plate holder 134 can be pulled in the proximal direction to force the fingers 350 out of engagement with the spinal plate 112 and to slide the plate holder 134 over the shaft 152 of the connector 150 and away from the surgical site. This can still leave the connector 150 connected to the interbody spacer as illustrated in FIG. 36.

Figure 38:
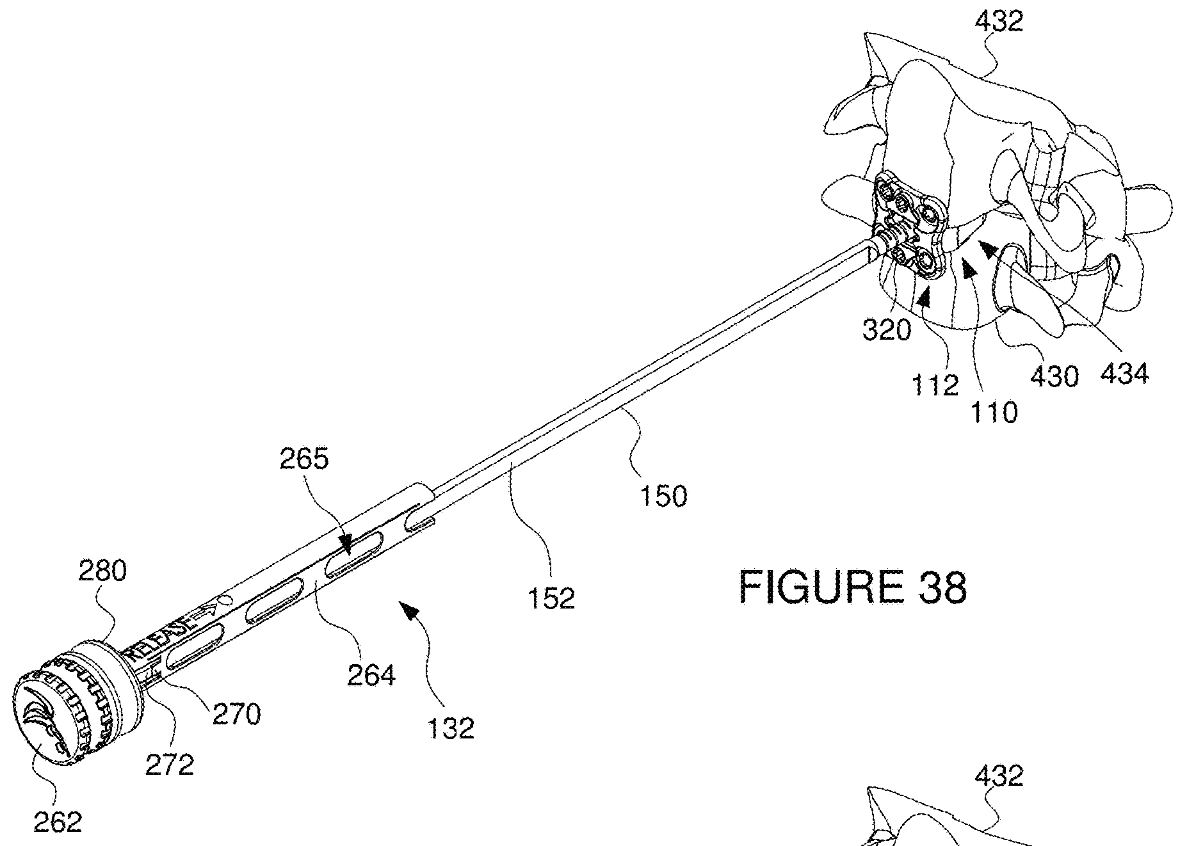
FIG. 38 is a view like FIG. 37 but with the lock ring moved to a locked position.
Figure 39:
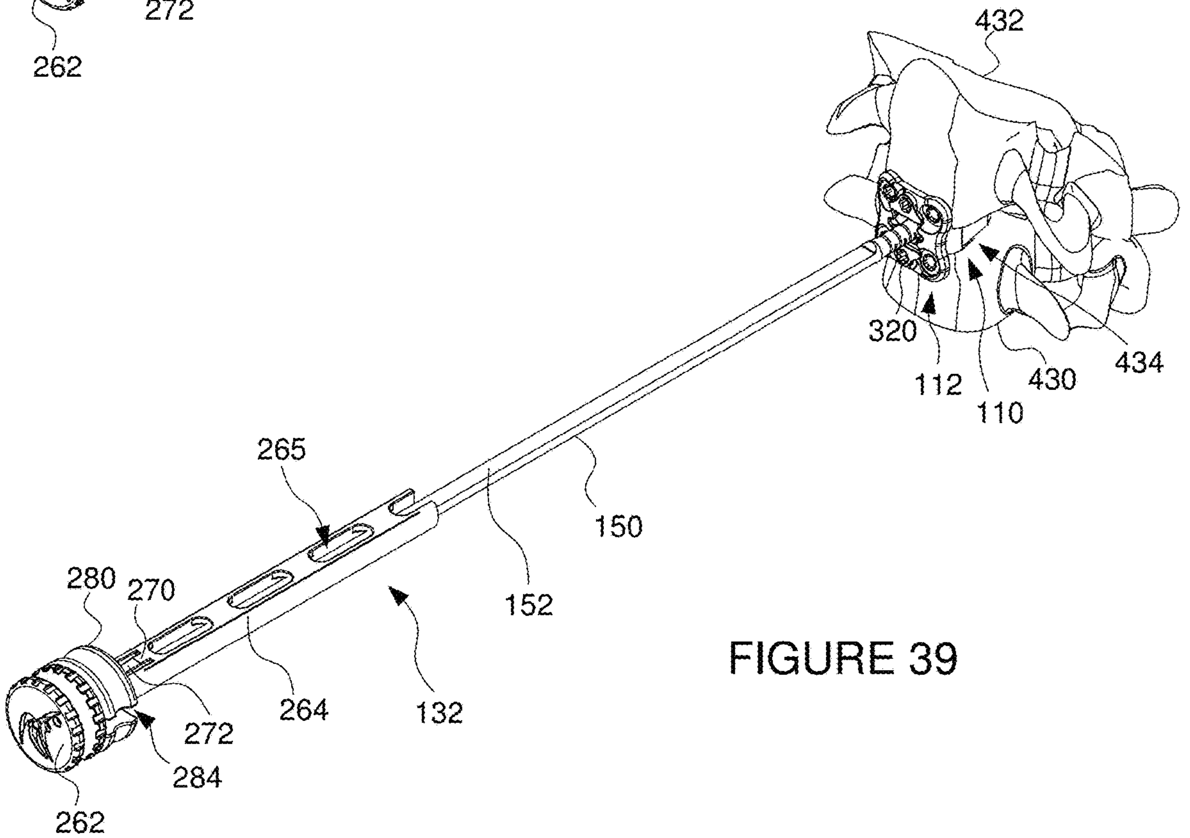
FIG. 39 is a view like FIG. 38 but with the extractor and the connector rotated to rotate the inserter to a disconnected position relative to the interbody spacer.
Figure 40:
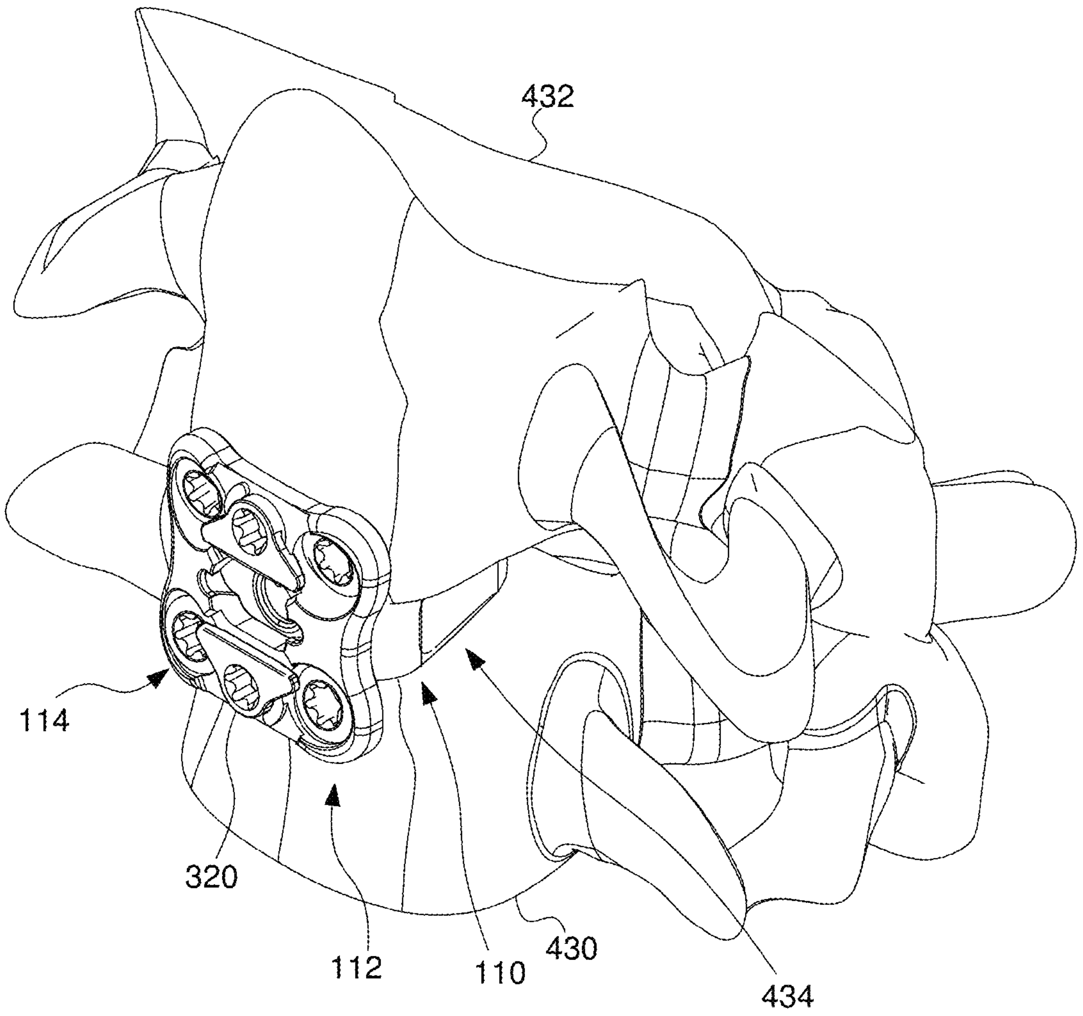
FIG. 40 is a view like FIG. 39 but with the extractor and the connector removed.

The extractor 132 can be used to extract the connector 150 from the surgical site. Specifically, the lock ring 280 of the extractor 132 can be slid to the unlocked position away from the handle 262, and the extractor 132 can be slid onto the shaft 152 of the connector 150 until the protrusion 274 of the latch 270 of the extractor 132 aligns with the securing hole 160 of the shaft 152, in the position illustrated in FIG. 37. The lock ring 280 can then be slid proximally to the locked position as illustrated in FIG. 38, so that the lock ring 280 pushes the latch 270 of the extractor 132 into the latched position discussed above with the protrusion 274 of the latch 270 entering the securing hole 160 and engaging the connector 150 to inhibit longitudinal sliding of the connector 150 and the extractor 132 relative to each other in the proximal-distal direction. The complimentary cross sections of the connector 150 and the extractor 132 can also inhibit rotation of the connector 150 and the extractor 132 relative to each other around the central longitudinal axis 176 (see FIG. 7) of the connector 150. Accordingly, the extractor 132 can be rotated in a counterclockwise direction when viewed in the distal direction to rotate the distal tip 154 of the connector 150 relative to the interbody spacer 110. This can rotate the protrusions 252 of the interbody spacer 110 out of the recesses 175 of the second slots 174 of the distal tip 154 and to the first slots 172 in the position illustrated in FIG. 39. The extractor 132 can then be pulled proximally to remove the distal tip 154 from the connection hole 250 of the interbody spacer 110 as the protrusions 252 slide out of the second slots of the distal tip 154. The extractor 132 and the connector 150 can then be extracted from the surgical site by continuing to pull the extractor 132 and therefore the connector 150 in the proximal direction. This can leave the implants including the interbody spacer 110, the spinal plate 112 and the screws 114 implanted as illustrated in FIG. 40. Post-implant procedures can then be performed for the surgical site.

The system components and techniques discussed herein are examples, and different techniques may be used in combination with these techniques and/or other techniques. Also, the subject matter defined in the appended claims is not necessarily limited to the benefits described herein. A particular implementation of the invention may provide all, some, or none of the benefits described herein. Although operations for the various techniques are described herein in a particular, sequential order for the sake of presentation, it should be understood that this manner of description encompasses rearrangements in the order of operations, unless a particular ordering is required. For example, operations described sequentially may in some cases be rearranged or performed concurrently. As a particular example, while the spinal implant technique discussed above is illustrated and described with reference to the inferior body 430, the superior body 432, and the interbody space 434, at least part of the technique described above with the implants and instruments adjacent to the inferior body 430 and superior body 432 could be performed without performance of a surgical procedure or prior to a surgical procedure. For example, the interbody spacer 110 may be prepared and positioned somewhere other than in the interbody space 434 (such as somewhere outside a living body) while the inserter housing 180 is removed from the connector 150 and the spinal plate 112 is then slid along the connector 150 toward the interbody spacer 110, as illustrated in FIG. 25 to FIG. 30 and FIG. 34 (except without the use of the awl 136 and awl guide 138 prior to a surgical procedure). The assembled interbody spacer 110 and spinal plate 112 could then be inserted into the area of the inferior body 430, the superior body 432, and the interbody space 434 using the connector 150 and the plate holder 134, with the interbody spacer 110 being inserted into the interbody space 434 and the spinal plate 112 being pressed against the inferior body 430 and the superior body 432. Techniques described herein with reference to flowcharts may be used with one or more of the systems described herein and/or with one or more other systems. Moreover, for the sake of simplicity, flowcharts may not show the different ways in which particular techniques can be used in conjunction with other techniques.

III. Example Aspects of the Disclosure

Some aspects of the disclosure will now be discussed. In these aspects, features of implementations of the aspects may be combined together with the general aspects and with each other in any combination not precluded by specific language or by the nature of the features and aspects. Indeed, features of each of the aspects can be used in combination with the features of the other aspects discussed herein. Some aspects discussed herein and elsewhere in this disclosure can involve techniques. Each of the acts in these techniques can be performed using the interbody spinal implant system or kit of parts discussed herein. Indeed, the interbody spinal implant system or kit of parts discussed herein can be configured to perform the acts of the techniques, as discussed herein. Also, the spinal implant system or kit of parts can include means for performing each of the acts discussed in the context of these techniques (such as via the components of the spinal implant system or kit of parts discussed herein), in different combinations.

Figure 41:
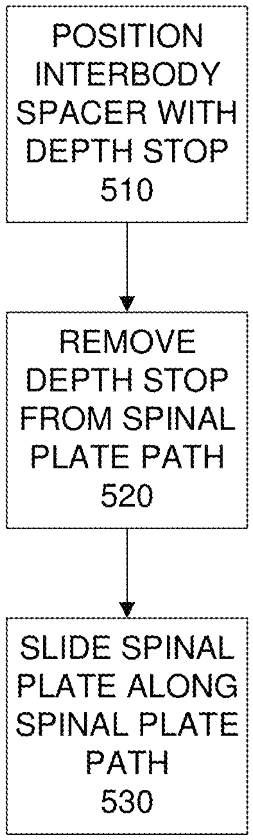
FIG. 41 is a flowchart of a spinal interbody spinal implant technique.

According to a first aspect and referring to FIG. 41, a spinal interbody spacer can be positioned 510 using a spinal interbody implant inserter including a spinal interbody implant connector and a depth stop while the interbody implant connector is connected to the interbody spacer and while the depth stop is connected to the interbody implant connector. The depth stop can inhibit over insertion of the interbody spacer. After positioning the interbody spacer, the depth stop can be removed 520 from a spinal plate path that extends along the interbody implant connector. The spinal plate can be slid 530 along the spinal plate path toward the interbody spacer while the interbody spacer is connected to the interbody implant connector and the depth stop is removed from the spinal plate path. Combinations of the features of the first aspect discussed in this paragraph can be used with each other and/or with features of the first aspect discussed in other paragraphs in any combination.

Also, the removing 520 of the depth stop from the spinal plate path can include disconnecting the depth stop from the interbody implant connector. The removing 520 of the depth stop can further include moving the depth stop away from the interbody implant connector. Combinations of the features of the first aspect discussed in this paragraph can be used with each other and/or with features of the first aspect discussed in other paragraphs in any combination.

The sliding 530 of the spinal plate can include using a plate holder to hold the spinal plate and slide the spinal plate along the interbody implant connector toward the interbody spacer. Also, the sliding 530 may include sliding along a central axis, and the plate holder can inhibit rotation of the interbody implant connector and the spinal plate around the axis relative to the plate holder while sliding the spinal plate along the interbody implant connector toward the interbody spacer. The axis can be a first axis, and the spinal plate can be rotated relative to the interbody implant connector along a second axis that is different from the first axis while the spinal plate is held by the plate holder with the plate holder being positioned along the interbody implant connector. Combinations of the features of the first aspect discussed in this paragraph can be used with each other and/or with features of the first aspect discussed in other paragraphs in any combination.

Additionally, the interbody implant connector can be connected to the interbody spacer. The connecting of the interbody implant connector to the interbody spacer can include inserting a tip of the interbody implant connector into the interbody spacer in a disconnected position and rotating the interbody implant connector (such as rotating less than one hundred and eighty degrees) relative to the interbody spacer to a rotational stop at a set connected position. A spring can bias the interbody implant connector to stay in the connected position. Combinations of the features of the first aspect discussed in this paragraph can be used with each other and/or with features of the first aspect discussed in other paragraphs in any combination.

Also, the positioning of the interbody spacer can include positioning the interbody spacer in a spinal interbody space between vertebral bodies. The depth stop can inhibit over insertion of the interbody spacer in the interbody space during the positioning of the interbody spacer. Also, the spinal plate can be secured to the vertebral bodies. Combinations of the features of the first aspect discussed in this paragraph can be used with each other and/or with features of the first aspect discussed in other paragraphs in any combination.

Also, a fastener can be positioned through a hole in the spinal plate, and a stop of the spinal plate can be rotated relative to a body of the spinal plate from a set rotational unlocked position to a set rotational locked position, with the stop inhibiting backout of the fastener through the hole in the spinal plate when the stop is in the set rotational locked position but not when the stop is in the set rotational unlocked position. The rotating of the stop can include rotating the stop from the set rotational unlocked position until reaching a rotational block of the stop at the set rotational locked position. Also, the rotating of the stop can include rotating the stop from the set rotational locked position until reaching another rotational block of the stop at the set rotational unlocked position. Combinations of the features of the first aspect discussed in this paragraph can be used with each other and/or with features of the first aspect discussed in other paragraphs in any combination.

According to a second aspect, a spinal interbody implant inserter system or kit of parts can include a spinal interbody spacer and a spinal interbody implant inserter. The interbody implant inserter can include a spinal interbody implant connector that is configured to be removably connected to the interbody spacer and a depth stop that is configured to be removably connected to the interbody implant connector while the interbody implant connector is removably connected to the interbody spacer. The depth stop and the interbody implant connector can be configured for the depth stop to be removed from the interbody implant connector while the interbody implant connector remains connected to the interbody spacer. The system or kit of parts can also include a spinal plate that is configured to slide along the interbody implant connector toward the interbody spacer while the interbody implant connector is connected to the interbody spacer. Combinations of the features of the second aspect discussed in this paragraph can be used with each other and/or with features of the second aspect discussed in other paragraphs in any combination.

The system or kit of parts may also include a plate holder that is configured to hold the spinal plate while the interbody implant connector is connected to the interbody spacer and while the spinal plate and the plate holder slide along the interbody implant connector toward the interbody spacer. The plate holder can include a sleeve that is configured to extend around the interbody implant connector while sliding along the interbody implant connector. The plate holder can include fingers that are configured to extend into an aperture in the spinal plate and to be biased away from each other to hold the spinal plate. The plate holder and the interbody implant connector can be configured to inhibit rotation between the plate holder and the interbody implant connector around a central axis, and between the plate holder and the spinal plate around the axis. Combinations of the features of the second aspect discussed in this paragraph can be used with each other and/or with features of the second aspect discussed in other paragraphs in any combination.

The system or kit of parts can also include an extractor that is configured to be removably connected to the interbody implant connector. The extractor can be configured to facilitate disconnecting the interbody implant connector from the interbody spacer. Combinations of the features of the second aspect discussed in this paragraph can be used with each other and/or with features of the second aspect discussed in other paragraphs in any combination.

The interbody implant connector can be configured to rotate (such as rotating less than one hundred and eighty degrees) relative to the interbody spacer from a disconnected position to a rotational stop at a set connected position. For example, the interbody implant connector can be configured to rotate about one quarter of a turn relative to the interbody spacer between the connected position and the disconnected position. The interbody implant connector can include a spring that biases the interbody implant connector to remain in the connected position. The interbody implant connector can be configured to rotate relative to the interbody spacer around a central axis between the connected position and the disconnected position, and the spring can be configured to exert a force between the interbody implant connector and the interbody spacer along the axis. Combinations of the features of the second aspect discussed in this paragraph can be used with each other and/or with features of the second aspect discussed in other paragraphs in any combination.

The depth stop can be removably connected to the interbody implant connector and the interbody implant connector can be removably connected to the interbody spacer. Combinations of the features of the second aspect discussed in this paragraph can be used with each other and/or with features of the second aspect discussed in other paragraphs in any combination.

Also, the spinal plate can be configured to receive a fastener through a hole in the spinal plate. The spinal plate can be configured to allow a stop of the spinal plate to be rotated relative to a body of the spinal plate from an unlocked position to a locked position, with the spinal plate being configured so that the stop inhibits backout of the fastener through the hole in the spinal plate when the stop is in a set rotational locked position. The spinal plate can be configured to allow rotation of the stop between the locked position and a set rotational unlocked position where the stop does not inhibit backout of the fastener. A rotational block can block further rotation of the stop in a first rotational direction at the set rotational locked position. Also, a rotational block can block further rotation of the stop in an opposite second rotational direction (opposite to the first rotational direction) at the set rotational unlocked position. Combinations of the features of the second aspect discussed in this paragraph can be used with each other and/or with features of the second aspect discussed in other paragraphs in any combination.

According to a third aspect, a spinal interbody inserter system or kit of parts can include a spinal interbody spacer and a spinal interbody implant inserter that is configured to be removably connected to the interbody spacer. The system or kit of parts can also include a spinal plate that is configured to slide along a spinal interbody implant connector of the interbody implant inserter toward the interbody spacer while the interbody implant connector is connected to the interbody spacer. The system or kit of parts can also include a plate holder that is configured to hold the spinal plate while the interbody implant inserter is connected to the interbody spacer and the spinal plate is sliding toward the interbody spacer along a central axis that extends along the interbody implant connector. The plate holder can be configured to inhibit rotation of the plate holder around the axis relative to the interbody implant connector and relative to the spinal plate. Combinations of the features of the third aspect discussed in this paragraph can be used with each other and/or with features of the third aspect discussed in other paragraphs in any combination.

The axis can be a first axis. Also, the spinal plate, the interbody implant connector, and the plate holder can be configured to allow limited rotation of the spinal plate relative to the interbody implant connector along a second axis that is different from the first axis while the spinal plate is held by the plate holder with the plate holder being positioned along the interbody implant connector. Combinations of the features of the third aspect discussed in this paragraph can be used with each other and/or with features of the third aspect discussed in other paragraphs in any combination.

According to a fourth aspect, a spinal interbody implant connector can be removably connected to a spinal interbody spacer. A spinal plate can slide along the interbody implant connector toward the interbody spacer while the interbody implant connector is connected to the interbody spacer. A plate holder can hold the spinal plate while the interbody implant connector is connected to the interbody spacer and the spinal plate is sliding toward the interbody spacer along a central axis that extends along the interbody implant connector. The plate holder can inhibit rotation of the plate holder around the axis relative to the interbody implant connector and relative to the spinal plate. Combinations of the features of the fourth aspect discussed in this paragraph can be used with each other in any combination.

According to a fifth aspect, a spinal interbody implant inserter system or kit of parts can include a spinal interbody spacer, a spinal interbody implant inserter, and a spinal plate. The interbody implant inserter can include a spinal interbody implant connector that is configured to be removably connected to the interbody spacer. The interbody implant connector can be configured to rotate around an axis relative to the interbody spacer from a disconnected position to a rotational stop at a set connected position where the interbody implant connector is connected to the interbody spacer. Combinations of the features of the fifth aspect discussed in this paragraph can be used with each other and/or with features of the fifth aspect discussed in other paragraphs in any combination.

The system or kit of parts can include a spring that is configured to bias the interbody implant connector and the interbody spacer toward remaining in the set connected position. Combinations of the features of the fifth aspect discussed in this paragraph can be used with each other and/or with features of the fifth aspect discussed in other paragraphs in any combination.

The spring can be configured to bias the interbody implant connector and the interbody spacer in a direction parallel or substantially parallel to the axis. Combinations of the features of the fifth aspect discussed in this paragraph can be used with each other and/or with features of the fifth aspect discussed in other paragraphs in any combination.

The spinal plate can be configured to slide along the interbody implant connector toward the interbody spacer while the interbody implant connector is connected to the interbody spacer. Combinations of the features of the fifth aspect discussed in this paragraph can be used with each other and/or with features of the fifth aspect discussed in other paragraphs in any combination.

The interbody spinal implant inserter system or kit of parts can be configured to inhibit rotation of the spinal plate relative to the interbody implant connector around the axis (such as by being inhibited via the plate holder). Combinations of the features of the fifth aspect discussed in this paragraph can be used with each other and/or with features of the fifth aspect discussed in other paragraphs in any combination.

According to a sixth aspect, a technique can include removably connecting a spinal interbody implant connector to a spinal interbody spacer. The removably connecting can include rotating the interbody implant connector around an axis relative to the interbody spacer from a disconnected position to a rotational stop at a set connected position where the interbody implant connector is connected to the interbody spacer. Combinations of the features of the sixth aspect discussed in this paragraph can be used with each other and/or with features of the sixth aspect discussed in other paragraphs in any combination. The features of the sixth aspect discussed in this paragraph can be performed entirely outside of a living body, and they may be performed by personnel other than a medical practitioner performing a surgical technique.

The technique may include biasing the interbody implant connector and the interbody spacer toward remaining in the set connected position using a spring. For example, the spring may bias the interbody implant connector and the interbody spacer in a direction parallel or at least substantially parallel to the axis. Combinations of the features of the sixth aspect discussed in this paragraph can be used with each other and/or with features of the sixth aspect discussed in other paragraphs in any combination. The features of the sixth aspect discussed in this paragraph can be performed entirely outside of a living body, and they may be performed by personnel other than a medical practitioner performing a surgical technique.

The technique may also include sliding a spinal plate along the interbody implant connector toward the interbody spacer while the interbody implant connector is connected to the interbody spacer. Combinations of the features of the sixth aspect discussed in this paragraph can be used with each other and/or with features of the sixth aspect discussed in other paragraphs in any combination.

Also, rotating the interbody implant connector relative to the interbody spacer can include rotating less than one hundred and eighty degrees, such as about one-quarter turn. Combinations of the features of the sixth aspect discussed in this paragraph can be used with each other and/or with features of the sixth aspect discussed in other paragraphs in any combination. The features of the sixth aspect discussed in this paragraph can be performed entirely outside of a living body, and they may be performed by personnel other than a medical practitioner performing a surgical technique.

Also, rotation of the spinal plate relative to the interbody implant connector around the axis can be inhibited, such as being inhibited by a plate holder that engages the spinal plate and the interbody implant connector. Combinations of the features of the sixth aspect discussed in this paragraph can be used with each other and/or with features of the sixth aspect discussed in other paragraphs in any combination.

According to a seventh aspect, a system or kit of parts can include a plate holder and a held plate that is either a spinal plate template or a spinal plate. The plate holder can be configured to removably hold the held plate with fingers of the plate holder being biased in opposite directions to grasp the held plate. Combinations of the features of the seventh aspect discussed in this paragraph can be used with each other and/or with features of the seventh aspect discussed in other paragraphs in any combination.

The system or kit of parts may include the plate holder holding the held plate with fingers of the plate holder being biased in opposite directions to grasp the held plate. In one example, the held plate may be a spinal plate template, and in another example, the held plate may be a spinal plate. Also, in one example, the plate holder can be configured to removably hold the held plate with fingers of the plate holder being biased outwardly away from each other to grasp the held plate. Also, the plate holder can include an internal channel that is configured to receive a shaft of a connector that is configured to be connected to a spinal interbody spacer. Combinations of the features of the seventh aspect discussed in this paragraph can be used with each other and/or with features of the seventh aspect discussed in other paragraphs in any combination.

According to an eighth aspect, a technique can include removably holding either a spinal plate template or a spinal plate using a plate holder. The removably holding can include moving the plate holder in a holder insertion direction until fingers of the plate holder are positioned to grasp the held plate, with the fingers being biased opposite each other to press against the plate and grasp the held plate. Combinations of the features of the eighth aspect discussed in this paragraph can be used with each other and/or with features of the eighth aspect discussed in other paragraphs in any combination. The features of the eighth aspect discussed in this paragraph can be performed entirely outside of a living body, and they may be performed by personnel other than a medical practitioner performing a surgical technique.

The held plate can be a spinal plate or a spinal plate template. In an example where the held plate is a spinal plate template and the holder insertion direction can be a first holder insertion direction, the technique can further include removably connecting the plate holder to a spinal plate. The removably connecting to the spinal plate can include moving the plate holder in a second holder insertion direction (that may or may not be the same as the first holder insertion direction) until the fingers of the plate holder are positioned to grasp the spinal plate, with the fingers being biased opposite each other to press against the spinal plate and grasp the spinal plate. Combinations of the features of the eighth aspect discussed in this paragraph can be used with each other and/or with features of the eighth aspect discussed in other paragraphs in any combination. The features of the eighth aspect discussed in this paragraph can be performed entirely outside of a living body, and they may be performed by personnel other than a medical practitioner performing a surgical technique.

The biasing of the fingers opposite each other can include the fingers being biased away from each other to grasp the plate. Also, moving the plate holder in the holder insertion direction can include moving the plate holder in the holder insertion direction until the fingers enter one or more holes in the held plate. Combinations of the features of the eighth aspect discussed in this paragraph can be used with each other and/or with features of the eighth aspect discussed in other paragraphs in any combination. The features of the eighth aspect discussed in this paragraph can be performed entirely outside of a living body, and they may be performed by personnel other than a medical practitioner performing a surgical technique.

According to a ninth aspect, a spinal plate can be configured to receive a fastener through a hole in the spinal plate. The spinal plate can be configured to allow a stop of the spinal plate to be rotated relative to a body of the spinal plate from an unlocked position to a locked position, with the spinal plate being configured so that the stop inhibits backout of the fastener through the hole in the spinal plate when the stop is in a set rotational locked position. The spinal plate can be configured to allow rotation of the stop between the locked position and a set rotational unlocked position where the stop does not inhibit backout of the fastener. A rotational block can block further rotation of the stop in a first rotational direction at the set rotational locked position. Also, a rotational block can block further rotation of the stop in an opposite second rotational direction (opposite to the first rotational direction) at the set rotational unlocked position. Combinations of the features of the ninth aspect discussed in this paragraph can be used with each other in any combination.

Although subject matter has been described in language specific to features such as compositions of matter, structural features, and/or methodological acts, it is to be understood that the subject matter defined in the appended claims is not necessarily limited to the specific features described above. Rather, the specific features described above are disclosed as example forms of implementing the claims.

We claim:

1. A method comprising:

positioning a spinal interbody spacer using a spinal interbody implant inserter comprising a spinal interbody implant connector and a depth stop while the interbody implant connector is connected to the interbody spacer and while the depth stop is connected to the interbody implant connector;

after the positioning of the interbody spacer, removing the depth stop from a spinal plate path that extends along the interbody implant connector while the interbody spacer is connected to the interbody implant connector; and after the removing of the depth stop, sliding a spinal plate along the spinal plate path toward the interbody spacer while the interbody spacer is connected to the interbody implant connector and the depth stop is removed from the spinal plate path.

2. The method of claim 1, wherein removing the depth stop from the spinal plate path comprises disconnecting the depth stop from the interbody implant connector.

3. The method of claim 2, wherein removing the depth stop further comprises moving the depth stop away from the interbody implant connector.

4. The method of claim 1, wherein sliding the spinal plate comprises using a plate holder to hold the spinal plate and slide the spinal plate along the interbody implant connector toward the interbody spacer.

5. The method of claim 4, wherein the sliding comprises sliding along a central axis, and wherein the plate holder inhibits rotation of the interbody implant connector and the spinal plate around the axis relative to the plate holder while sliding the spinal plate along the interbody implant connector toward the interbody spacer.

6. The method of claim 1, further comprising connecting the interbody implant connector to the interbody spacer, the connecting of the interbody implant connector to the interbody spacer comprising inserting a tip of the interbody implant connector into the interbody spacer in a disconnected position and rotating the interbody implant connector relative to the interbody spacer from the disconnected position to a rotational stop at a set connected position.

7. The method of claim 1, wherein the positioning of the interbody spacer comprises positioning the interbody spacer in a spinal interbody space between vertebral bodies, wherein the depth stop inhibits over insertion of the interbody spacer in the interbody space during the positioning of the interbody spacer, and wherein the method further comprises securing the spinal plate to the vertebral bodies.

8. A method comprising:

positioning a spinal interbody spacer using a spinal interbody implant inserter comprising a spinal interbody implant connector and a depth stop while the interbody implant connector is connected to the interbody spacer and while the depth stop is connected to the interbody implant connector;

after positioning the interbody spacer, removing the depth stop from a spinal plate path that extends along the interbody implant connector; and sliding a spinal plate along the spinal plate path toward the interbody spacer while the interbody spacer is connected to the interbody implant connector and the depth stop is removed from the spinal plate path;

wherein sliding the spinal plate comprises using a plate holder to hold the spinal plate and slide the spinal plate along the interbody implant connector toward the interbody spacer;

wherein the sliding comprises sliding along a central axis, and wherein the plate holder inhibits rotation of the interbody implant connector and the spinal plate around the axis relative to the plate holder while sliding the spinal plate along the interbody implant connector toward the interbody spacer; and wherein the axis is a first axis, and wherein the method further comprises rotating the spinal plate relative to the interbody implant connector along a second axis that is different from the first axis while the spinal plate is held by the plate holder with the plate holder being positioned along the interbody implant connector.

9. The method of claim 8, wherein removing the depth stop from the spinal plate path comprises disconnecting the depth stop from the interbody implant connector.

10. The method of claim 9, wherein removing the depth stop further comprises moving the depth stop away from the interbody implant connector.

11. The method of claim 8, further comprising connecting the interbody implant connector to the interbody spacer, the connecting of the interbody implant connector to the interbody spacer comprising inserting a tip of the interbody implant connector into the interbody spacer in a disconnected position and rotating the interbody implant connector relative to the interbody spacer from the disconnected position to a rotational stop at a set connected position.

12. The method of claim 11, wherein a spring biases the interbody implant connector to stay in the connected position.

13. The method of claim 8, wherein the positioning of the interbody spacer comprises positioning the interbody spacer in a spinal interbody space between vertebral bodies, wherein the depth stop inhibits over insertion of the interbody spacer in the interbody space during the positioning of the interbody spacer, and wherein the method further comprises securing the spinal plate to the vertebral bodies.

14. A method comprising:

positioning a spinal interbody spacer using a spinal interbody implant inserter comprising a spinal interbody implant connector and a depth stop while the interbody implant connector is connected to the interbody spacer and while the depth stop is connected to the interbody implant connector;

after positioning the interbody spacer, removing the depth stop from a spinal plate path that extends along the interbody implant connector;

sliding a spinal plate along the spinal plate path toward the interbody spacer while the interbody spacer is connected to the interbody implant connector and the depth stop is removed from the spinal plate path; and connecting the interbody implant connector to the interbody spacer, the connecting of the interbody implant connector to the interbody spacer comprising inserting a tip of the interbody implant connector into the interbody spacer in a disconnected position and rotating the interbody implant connector relative to the interbody spacer from the disconnected position to a rotational stop at a set connected position, wherein a spring biases the interbody implant connector to stay in the connected position.

15. The method of claim 14, wherein removing the depth stop from the spinal plate path comprises disconnecting the depth stop from the interbody implant connector.

16. The method of claim 15, wherein removing the depth stop further comprises moving the depth stop away from the interbody implant connector.

17. The method of claim 14, wherein sliding the spinal plate comprises using a plate holder to hold the spinal plate and slide the spinal plate along the interbody implant connector toward the interbody spacer.

18. The method of claim 17, wherein the sliding comprises sliding along a central axis, and wherein the plate holder inhibits rotation of the interbody implant connector and the spinal plate around the axis relative to the plate holder while sliding the spinal plate along the interbody implant connector toward the interbody spacer.

19. The method of claim 14, wherein the positioning of the interbody spacer comprises positioning the interbody spacer in a spinal interbody space between vertebral bodies, wherein the depth stop inhibits over insertion of the interbody spacer in the interbody space during the positioning of the interbody spacer, and wherein the method further comprises securing the spinal plate to the vertebral bodies.

* * * * *